(12) United States Patent
Burke et al.

(10) Patent No.: US 10,359,390 B2
(45) Date of Patent: Jul. 23, 2019

(54) SYSTEMS AND METHODS TO COMPENSATE FOR SOURCES OF ERROR DURING ELECTROCHEMICAL TESTING

(71) Applicant: Roche Diabetes Care, Inc., Indianapolis, IN (US)

(72) Inventors: David W. Burke, Indianapolis, IN (US); Michael Marquant, Mannheim (DE); Nigel A. Surridge, Indianapolis, IN (US)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 661 days.

(21) Appl. No.: 13/920,183

(22) Filed: Jun. 18, 2013

(65) Prior Publication Data

US 2013/0277234 A1    Oct. 24, 2013

Related U.S. Application Data

(63) Continuation of application No. PCT/EP2011/006429, filed on Dec. 20, 2011.

(60) Provisional application No. 61/426,062, filed on Dec. 22, 2010.

(51) Int. Cl.
*G01N 27/327* (2006.01)

(52) U.S. Cl.
CPC ................................ *G01N 27/3274* (2013.01)

(58) Field of Classification Search
CPC .............. A61B 5/1486; A61B 5/14532; A61B 5/14535; A61B 2562/0295; G01N 27/327–27/3274
See application file for complete search history.

(56) References Cited

U.S. PATENT DOCUMENTS

| | | | |
|---|---|---|---|
| 6,645,368 B1 * | 11/2003 | Beaty et al. | 205/792 |
| 2004/0157337 A1 | 8/2004 | Burke et al. | |
| 2010/0084268 A1 * | 4/2010 | Pierce | C12Q 1/004 204/403.14 |
| 2010/0170807 A1 | 7/2010 | Diebold et al. | |
| 2011/0139634 A1 * | 6/2011 | Chou | G01N 27/3274 205/792 |
| 2011/0162978 A1 * | 7/2011 | Cardosi et al. | 205/777.5 |
| 2012/0080323 A1 * | 4/2012 | Chatelier | C12Q 1/005 205/775 |

FOREIGN PATENT DOCUMENTS

| | | |
|---|---|---|
| EP | 1770396 A2 | 4/2007 |
| EP | 1839571 A1 | 10/2007 |
| WO | 1999/030152 A1 | 6/1999 |

(Continued)

*Primary Examiner* — Maris R Kessel
(74) *Attorney, Agent, or Firm* — Woodard, Emhardt, Henry, Reeves & Wagner, LLP

(57) ABSTRACT

A method is disclosed for determining analyte concentration that includes applying a first electrical potential excitation pulse to a body fluid sample in an analyte sensor, and a first current response of the body fluid sample to the first pulse is measured. A second excitation pulse is applied to the body fluid sample in the analyte sensor, and a second current response of the body fluid sample to the second pulse is measured. An analyte level in the body fluid sample is determined by compensating for sources of error based on the first current response to the first pulse.

27 Claims, 18 Drawing Sheets

(56) References Cited

FOREIGN PATENT DOCUMENTS

| | | |
|---|---|---|
| WO | 1999/032881 A1 | 7/1999 |
| WO | 2008/040998 A3 | 4/2008 |
| WO | 2009/015316 A1 | 1/2009 |
| WO | 2009/041782 A3 | 4/2009 |
| WO | 2011/121292 A1 | 10/2011 |

* cited by examiner

SYSTEMS AND METHODS TO COMPENSATE FOR SOURCES OF ERROR DURING ELECTROCHEMICAL TESTING

CROSS-REFERENCE TO RELATED APPLICATIONS

This patent application is a continuation of Int'l Patent Application No. PCT/EP2011/006429; filed Dec. 20, 2011, which claims the benefit of U.S. Provisional Patent Application No. 61/426,062; filed Dec. 22, 2010. Each patent application is incorporated herein by reference as if set forth in its entirety.

TECHNICAL FIELD

The invention relates generally to statistics and electrochemistry, and more particularly to methods of measuring the presence and/or concentration of an analyte in a biological fluid, and more specifically, but not exclusively, to methods that account for various sources of error such as variability of the reaction rate and/or presence of interfering signals during measurement of the analyte with an electrochemical biosensor.

BACKGROUND

Measuring the concentration of substances, particularly in the presence of other confounding substances and under varied conditions, is important in many fields such as medical diagnosis. For example, the measurement of glucose in body fluids, such as blood, is crucial to the effective treatment of diabetes.

Diabetic therapy typically involves two types of insulin treatment: basal and meal-time. Basal insulin treatment refers to continuous (e.g., time-released) insulin, often taken before bed. Meal-time insulin treatment provides additional dose boluses of faster-acting insulin to regulate fluctuations in blood glucose caused by a variety of factors, including the metabolization of sugars and carbohydrates. Proper regulation of blood glucose fluctuations requires accurate measurement of the concentration of glucose in the blood. Failure to do so can produce extreme complications, including blindness and loss of circulation in the extremities, which can ultimately deprive a diabetic of use of his or her fingers, hands, feet, etc.

Biosensor test strips often are used to measure the presence and/or concentrations of selected analytes in test samples. For example, a variety of test strips are used to measure glucose concentrations in blood to monitor the blood sugar level of diabetics. These test strips typically include a reaction chamber into which a reagent composition has been deposited. Current trends in test strips require smaller test samples and faster analysis times. This provides a significant benefit by allowing the use of smaller blood samples that can be obtained from less sensitive areas of the body, such as the forearm or the palm of the hand. Additionally, faster and more accurate test times provide better control of the diabetic's blood sugar level.

Multiple methods are known for measuring the concentration of analytes, such as glucose, in a blood sample. Such methods typically fall into one of two categories: optical methods and electrochemical methods. Optical methods generally involve reflectance or absorbance spectroscopy to observe a spectrum shift in a reagent. Such shifts are caused by a chemical reaction that produces a color change indicative of the concentration of the analyte. Electrochemical methods, however, generally involve amperometric, coulometric, potentiometric and/or conductive responses indicative of the concentration of the analyte. See, e.g., U.S. Pat. Nos. 4,233,029; 4,225,410; 4,323,536; 4,008,448; 4,654,197; 5,108,564; 5,120,420; 5,128,015; 5,243,516; 5,437,999; 5,288,636; 5,628,890; 5,682,884; 5,727,548; 5,997,817; 6,004,441; 4,919,770; 6,645,368; Re. 36,268 and 6,054,039.

In the consumer market segment, electrochemical methods typically use hand-held meters (but not always) to measure the electrochemical response of a blood sample in the presence of a reagent provided on a suitable biosensor. The reagent reacts with the glucose to produce charge carriers that are not otherwise present in the sample. Consequently, the electrochemical response of the blood is intended to be primarily dependent upon the concentration of blood glucose. Typical reagents used in electrochemical blood glucose meters and biosensors are disclosed in U.S. Pat. Nos. 5,997,817; 5,122,244; 5,286,362 and 7,727,467.

For example, biosensor test strips have been developed that employ the electrochemical principle of biamperometry. In one example, a biamperometric test strip contains the enzyme glucose dehydrogenase (GDH), which converts glucose in a blood sample to gluconolactone. This reaction liberates electrons that react with a mediator. In this example, an oxidized form of a mediator, such as hexacyanoferrate (III), accepts an electron and becomes a reduced form of the mediator, hexacyanoferrate (II). The meter applies a voltage between two electrodes, which causes the reduced mediator formed during a reaction incubation period to be reconverted to an oxidized mediator. This generates a small current that is read by the meter. One benefit is that biamperometric sensors do not require a true counter/reference electrode. Instead, the electrodes can be generally the same or substantially similar conductive materials, which in turn simplifies manufacturing of the test strip.

There are, however, a number of error sources that can create inaccurate results when measuring analyte levels in body fluid. For example, one issue with amperometric sensors is that the rate of reaction will affect the current response to a direct current (DC) potential measured at a predetermined time. Generally speaking, the reaction rate for a reactant or product in a particular reaction is traditionally defined as how fast a particular reaction takes place.

For amperometric tests, if the reaction rate is fast, then the current maximum and the measured current response may be higher than if the reaction rate is slow, even for sensors evaluating samples having the same concentration of analyte. For example, the reaction rate in an amperometric test is generally considered fast when the time to current maximum or peak current is less than that of other tests. Conversely, the reaction for a given amperometric test is typically considered slow when it takes longer to reach peak current in comparison to other tests. If the reaction rate is variable, then the current response at a given time will not be representative of an accurate measurement. As should be recognized, numerous factors can affect the reaction rate and its variability, such as temperature, diffusion rates and enzyme activity.

The effect of reaction rate is specifically important in the context of a fixed test time, such as those described herein, which are typical in systems used directly by consumers. For example, in the ACCU-CHEK® AVIVA® System employing a 5 to 6 second fixed test time, where the first 3 seconds constitute a fixed incubation time, the reaction is substantially complete by the time the measurement of glucose is made. In this system, an enzyme is employed such that the reaction is substantially complete under a wide variety of operating conditions such as temperature and aging of the test devices. As such, the enzyme is classified as "fast." The rate of reaction problem can be exacerbated when an enzyme with a lower specific activity than the "fast" enzyme mentioned above and/or low reaction velocity is employed in the biosensor such as that used in embodiments herein. Under certain operating conditions, such as when the test is performed with an ambient temperature of 6° C., the reaction is not substantially complete until 10 or more seconds, which renders a fixed test time format of 5 seconds highly inaccurate. Sometimes harsh conditions to which the biosensor sensor is exposed worsen its accuracy.

Occasionally, the biosensor test strip can experience harmful conditions, often termed "strip rotting" or "vial abuse," which refers to when the sensors are abused and exposed to detrimental conditions, such as excessive heat and/or moisture, during storage. This exposure to excessive heat and/or moisture also can result in slowing of the reaction times due to loss of enzyme activity leading to an inaccurate result using the fixed test time referred to above.

In the past, these issues have been avoided by using enzymes that have very fast reaction times and high specific activities with the analyte being measured. High loadings or amounts of enzymes in the biosensor also can help to avoid these reaction rate problems. By utilizing enzymes with these particular characteristics, reactions having high and similar levels of completion under all test conditions, such as at various temperatures and hematocrit levels, can be better achieved.

However, as a practical matter, some otherwise useful or desirable enzymes cannot be incorporated with high enough amounts into the biosensor without causing a significant loss in its performance. In addition, enzymes of high specific activities are not always desirable for all analytes. For example, many such systems are susceptible to adverse effects from various interfering substances (also referred to as non-analyte reacting compounds), such as maltose, galactose, xylose and the like, which can create inaccurate readings. Individuals undergoing peritoneal dialysis or Immunoglobulin G (IGG) therapy can experience high levels of maltose in their blood, which can interfere with accurate blood glucose readings. Therefore, interference from maltose can be a significant problem.

As an illustration, Abbott Laboratories' FREESTYLE® Blood Glucose Monitoring System employs a glucose-dye-oxidoreductase (GlucDOR) enzyme in conjunction with a coulometric technique with a variable test time to ensure robustness in view of varying degrees of reaction velocity. However, in addition to coulometry having a number of drawbacks making it impractical for many applications, such a system is still clinically unacceptable due to interference from maltose.

In addition to slowing enzyme activity, vial abuse also can result in an increase of background current, sometimes referred to as "blank current," when readings are taken. There are a variety of sources for background or blank current. For instance, it is often desirable that mediators, which are used to transfer electrons from the enzyme to the electrode, be in an oxidized state before the biosensor is used. Over time, heat and/or humidity from vial abuse will tend to reduce the mediator. If part of the mediator is in a reduced form before the biosensor is used, a portion of the current will result from the working electrode oxidizing the reduced form of the mediator. The resulting background or blank current will tend to bias the signal, which in turn can lead to inaccurate results. Impurities in the reagent also can increase background or blank current problems.

Yet another source of error is blank current derived from other interfering compounds present in the blood as opposed to originating in the reagent. Examples of such error sources include ascorbate and acetaminophen, both of which are electrochemically active (or "electroactive") and can react with either the electrode surface or the mediator used in the reagent layer. These and other compounds present in the fluid sample can contribute to a so-called blank current measured by the electrode that is not related to glucose concentration, and therefore provides a source of error.

Besides electroactive interfering compounds in the fluid sample itself, other interfering substances (such as non-analyte reacting compounds, the concentration of which may vary from sample to sample) can interact with various ingredients of the reagent and/or affect the manner in which the analyte diffuses. For example, GDH is an enzyme that catalyzes glucose, but also catalyzes other interfering substances, such as maltose, xylose, galactose and lactose. When the reagent used for the electrochemical testing includes GDH, the presence of one of these interfering sugars can adversely affect the measured glucose concentration. It also can be difficult to determine the concentrations of these interfering sugars prior to testing, and users who may have abnormal levels of such interfering sugars are frequently cautioned against using test strips with GDH. For example, disclaimers are used on many test strips with GDH reagents to assure that users with potential for abnormal levels of such interfering sugars do not test with GDH-based test strips.

As such, a need for reagent enzymes that are independent of those interfering sugars has been identified. However, some enzymes exhibiting this independence suffer from slow reactivity, which is a problem set forth and discussed above.

Interfering substances can occur naturally and can occur in varying concentrations in fluid samples. For example, the temperature of a fluid sample, or the concentration of red blood cells (hematocrit), uric acid, bilirubin or oxygen in body fluid can adversely influence the accuracy of blood glucose measurements.

Amperometric sensors have been proposed that use a "burn-off" approach to address at least some sources of the blank current problem. In this approach, two DC signals are applied to the sensor. The first DC signal, or burn-off signal, is used to consume or oxidize any species responsible for the blank current in the same diffusion layer adjacent to the working electrode that is later used to analyze the analyte. Afterwards, the second signal, or analysis signal, is used to analyze the analyte levels. Both the burn-off and analysis potentials have the same polarity and affect local concentrations of species at the same electrode and in a similar manner due to the common polarity. Although this burn-off technique reduces the effect of blank or background current, it does so at the expense of partially oxidizing (or reducing) the analyte to be measured, thereby reducing the signal-to-noise ratio of the sensor.

Algorithmic approaches in conjunction with the burn-off approach have been employed to define the relationship between burn-off current and measurement current produced by the respective two DC signals applied to the sensor. Nevertheless, such techniques have failed to compensate for variations in reaction time caused by factors such as enzymes with slow/variable reaction velocities. In addition, some enzymes used in such sensors, such as GDH, tend to be susceptible to maltose interference. Furthermore, such techniques require that the two signals are close enough in time such that additional reduced mediator does not diffuse back to the electrodes and effectively negate the reduction of blank and/or background current-causing species.

In contrast to GDH, glucose oxidase (GOx) exhibits a strong specificity for glucose and is generally maltose-independent. These features make GOx a suitable alternative to GDH when testing for glucose. However, GOx is an enzyme for which the natural terminal electron acceptor for glucose conversion is oxygen, and variations in the level of oxygenation of blood, such as is the case when comparing venous, arterial and capillary blood, can produce variations in the GOx response and can adversely affect the accuracy of glucose measurements using GOx.

A sharp relation between bias and blood oxygenation has been identified in GOx-based biosensors. As reflected in FIG. 1, the response bias (in milligrams per deciliter) varies considerably depending on the oxygenation of the sample (depicted in torr), and the measured glucose concentration can vary considerably depending on the oxygenation level of the sample when using GOx. See, e.g., FIGS. 2 and 3 depicting the test results of a biosensor using a GOx reagent that does not compensate for blood oxygenation. It was realized that test techniques are needed that accurately measure an analyte in a fluid, for example glucose in blood, in the presence of non-analyte reacting compounds.

For the foregoing reasons, it would be desirable for a sensor or measurement method to not be significantly affected by reaction time variability and to be insensitive to several sources of blank current. It also would be desirable if the sensor could be insensitive to both maltose levels and blood oxygen levels.

BRIEF SUMMARY

One aspect includes a method of determining analyte concentration. A first pulse of electrical excitation (preferably in the form of a direct current or DC pulse) can be applied to a body fluid sample in an analyte sensor, and a first response of the body fluid sample to the first pulse is measured. A second pulse of electrical excitation (also preferably in the form of a direct current or DC pulse) can be applied to the body fluid sample in the analyte sensor, and a second response of the body fluid sample to the second pulse is measured. An analyte level in the body fluid sample can be determined by compensating for reaction time and/or various sources of blank current based on the first response to the first pulse, preferably without the need to explicitly calculate the reaction time or specifically identify or measure the blank current of the sensor.

In another aspect, an amperometric sensor includes electrodes and a reagent covering the electrodes. The electrodes include a first electrode and a second electrode. A first DC pulse with a first polarity can be applied to the electrodes, and the first electrode acts as a first working electrode during the first DC pulse. A first amperometric response of the body fluid to the first DC pulse can be measured. A second DC pulse with a second polarity can be applied to the electrodes, and the second electrode acts as a second working electrode during the second DC pulse. The first polarity can be opposite the second polarity to lessen mediator or analyte depletion over the second electrode. A second amperometric response of the body fluid to the second DC pulse can be measured, and analyte concentration in the body fluid can be determined based on the first amperometric response and the second amperometric response.

In some embodiments, the absolute magnitude of both pulses should be sufficiently large so that the sources of the blank current and/or the sources of the glucose-related current (i.e., reduced mediator) can be oxidized by one or the other of the electrodes during the application of the pulses.

In other embodiments, the magnitude of one pulse can be different than the magnitude of the other pulse.

In other embodiments, the first pulse and second pulse can be separated in time by a period of reduced or zero potential, such as either an open cell or a fixed potential low enough so that no substantial oxidation is driven at any of the electrodes (an open cell condition as discussed herein).

In other embodiments, the first and second pulses can be applied generally one after the other with no period of an open cell condition therebetween.

In certain instances, it was discovered that the sensitivities of the first and second current responses (in particular DC responses) generally co-vary in a fixed proportion governed by the system diffusion while the offset in these relations differ depending upon the reaction time and/or the levels of the various sources of blank current present in the cell, from either the reagent or from the fluid sample itself. Thus, in another aspect, given two input measures of known relative analyte sensitivity but unknown offset (e.g., due to the level of blank current source in the cell), an algebraically constructed substitute for the current measure, which subtracts the offset can be substituted into the response algorithm and an improved glucose concentration can be calculated.

Other embodiments include an improved measurement sequence for detecting glucose in a blood sample with a glucose-specific enzyme with improved levels of oxygen insensitivity.

Other embodiments include a maltose-insensitive system and/or method for testing fluid, such as blood, for an analyte with improved accuracy for blood samples with various oxygenation levels, such as capillary, venous, arterial and neonatal blood.

In other embodiments, a linear correction of the DC current response is used in a GOx-based biosensor to correct for variations in blood oxygenation.

Other embodiments include applying a first DC voltage pulse to the test sample, measuring a response of the test sample to the first DC voltage pulse, applying a second DC voltage pulse to the test sample, measuring a response of the test sample to the second DC voltage pulse, and determining a correction by using the two responses in a mathematical algorithm.

In some embodiments, the DC current response is measured twice, once early in the test and once at a later time, and the applied DC excitation is changed in magnitude between measurement times, and the offset in response caused by the blood oxygenation variation is compensated for using a mathematical algorithm.

Embodiments also can be used in conjunction with other techniques that compensate for impedance influencers such as temperature and hematocrit. Such techniques include applying an electrical potential signal having an alternating current (AC) component to the sample. In one example, the signal with AC component is a low amplitude AC signal and is applied during a period between the first DC and second DC pulses.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
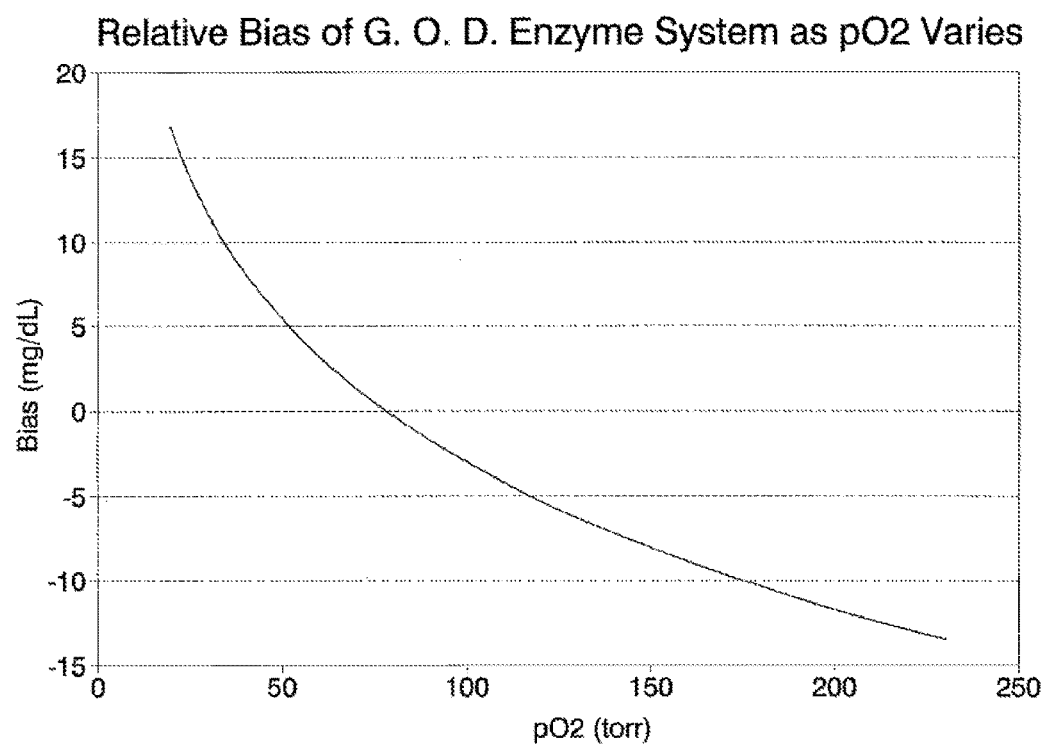
FIG. 1 shows the effect of the blood oxygenation level upon response bias, utilizing GOx (also referred to as GOD) as an enzyme.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The methods and systems now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the methods and systems described herein will come to mind to one of skill in the art having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Biosensors and Systems

A biosensor useful for the practice of embodiments described herein includes an electrochemical cell that includes spaced-apart working and counter electrodes and a redox reagent system. At least two electrical potentials are applied to the electrodes and the sample to determine a compensated level of an analyte of interest in the sample, such as glucose concentration in a blood sample. While the subject methods may be used, in principle, with any type of electrochemical cell having spaced-apart working and counter electrodes and a redox reagent system configured for electrochemically determining concentration of the analyte, in many embodiments the subject methods employ an electrochemical test strip.

Such electrochemical test strips are made up of two opposing substrates separated by a thin spacer layer, where these components define a reaction area or zone in which is located a redox reagent system. Present in the reaction area is a redox reagent system, which reagent system generates a reduced reaction product that is oxidized at an electrode in the reaction area when a suitable electrical potential excitation is applied. The amount of reduced reaction product generated is measured as correlating to the measured current in response to the electrical potential, and is used to derive the concentration of analyte of the biological fluid. The redox reagent system present in the reaction area typically includes at least an enzyme with specificity for the analyte of interest. A mediator also may be included as needed or desired to enhance the transfer of electrons from the analyte to an electrode during the reaction process. In many embodiments, the enzyme member of the redox reagent system is an enzyme or a plurality of enzymes that work in concert to oxidize the analyte of interest. As disclosed herein, GDH and GOx were each used as an enzyme for measuring concentration of glucose in blood samples. It is noted, however, that the present invention is not limited to these enzymes but instead is useful for any enzyme of a redox reagent system that introduces sources of error that will need correction in the determination of the concentration of the analyte being tested.

Typically, GDH is oxygen-independent, but in its natural state is susceptible to maltose sensitivity. Mutated GDH enzymes address the maltose sensitivity, but many have been discovered to have much slower reaction kinetics. In contrast, GOx is typically maltose-insensitive, but results in bias based on oxygenation levels in the fluid sample, such as whole blood.

More specifically, a cell for receiving a fluid sample is provided. The cell supports a chemistry that reacts with the fluid sample. Further in the cell are first and second terminals across which the reaction of the fluid sample can be analyzed. A test sample of the fluid sample is provided to the cell. A further instrument is provided that has first and second terminals corresponding to the first and second terminals in the cell. The first and second terminals, respectively, of the instrument are placed such that they are in contact with the first and second terminals of the cell, respectively, and in a position to allow the instrument to analyze the reaction. Included in the instrument is a controller, which applies a voltage between the first and second terminals of the instrument. One or more current responses from the applied voltage potential are measured at one or more predetermined times, and these current responses are used to determine the presence and/or concentration of the analyte of interest.

The voltage potentials applied to the test sample include, in certain embodiments, a first potential applied at a first time and a second potential applied at a second time. In one embodiment, the first potential and second potential have different absolute magnitudes. In other embodiments, the absolute magnitudes are substantially the same. The sample's current response to the first applied potential is measured, and the sample's current response to the second applied potential is measured, resulting in a first response and a second response. The sensitivities of the current responses to the analyte for the first and second responses have been found to co-vary in a fixed proportion that is governed by the system diffusion. The offsets in these relations, however, differ depending on the particular sources of error in the detection system, including sources of error in the redox reagent system and the sample itself. The offsets in these relations, while unknown, are constructed by (i) using the two given input measures of the applied electrical potentials having known analyte (e.g., glucose) sensitivity relative to the redox reagent system, and by (ii) using an algebraically constructed substitute for the measure of current response, which subtracts the offset based on the error sensitivity and is inserted into an algorithm used to determine the concentration of the analyte. Separating the applications of the two potentials in time and/or magnitude allows the relative influence of the error source (e.g., blood oxygenation ($pO_2$)) to be sufficiently different for calculation of a correction.

As described in more detail below, one embodiment generally concerns a method of amperometric determination of the concentration of an analyte such as glucose, particularly using analyte-specific enzymes that have a slow and variable reaction velocity (i.e., a reaction velocity that is slow and varies over time) and a method of amperometric determination of the concentration of said analyte in the presence of other blank current sources.

In an exemplary embodiment, the "slow" enzyme is mutated PQQ-dependent GDH as described in U.S. Pat. Nos. 7,732,179; 7,547,535 and 7,547,524. As previously noted, one problem is that the rate of reaction will affect the sample's current response to a DC potential measured at a predetermined time. For example, if the reaction rate is fast, then the current maximum and the measured current response may be higher than if the reaction rate is slow, even for sensors evaluating samples having the same concentration of analyte.

In prior art systems for which the reaction rate of the enzyme is sufficiently fast, test strips containing enzyme amounts above a certain threshold give an invariant response even as some enzyme activity is lost due to aging or abuse as described previously. Typically, test strips are constructed with enzyme amounts above this critical threshold. In the case of some enzymes exhibiting slow reaction rates, it is not possible to construct a test strip with sufficient enough enzyme to display this invariant response as the sensor ages. Therefore, the reaction rate of these sensors can vary as a function of, for example, age, exposure to harsh conditions, or anything that causes the activity of the enzyme to change. If the reaction rate varies over a wide range, then the current response at a given time will not be representative of the actual analyte concentration because the reaction is not complete. However, if it is possible to compensate for this variability in reaction rate, then a correction factor can be applied and an accurate reading can be obtained. Although the methods described below reference analyzing blood glucose levels, it should be recognized that other types of analytes can be analyzed with these techniques and that other types of enzymes can be used that also may be described as "slow" in accordance with this disclosure.

As will be explained in greater detail below, to compensate for sources of error, such as rate of reaction and blank current variations, successive electrical potential pulses are applied to the fluid sample. The first pulse may be provided soon after sample application and is used to evaluate one or both of the "rate of reaction" based on the shape and time-to-current-maximum of the current response and the presence and/or level of bias from blank current sources. The second pulse forms the primary basis for the analyte measurement, and it is compensated by the signal response measured for the first pulse.

With respect to a glucose test, for example, this allows for the combination of enzyme specificity and a sensor that is both maltose and blood oxygen insensitive. In one instance, this allows for the use of a very analyte-specific and oxygen-insensitive enzyme, whose very specificity results in slow reaction rate incurring the need for compensation. In another instance, this allows for the use of an analyte-specific enzyme exhibiting oxygen interference in conventional systems and methods. There can be numerous variations on this technique. For example, in one variation the total test time is fixed, and the information from the first current measurement is used in compensating for the interferent and error source issues in the second current measurement.

In one embodiment, other blank current sources comprise electrochemical interferents present in the sample itself such as ascorbate in blood. To one of skill in the art, this is a well-known source of blank current in blood samples analyzed with electrochemical biosensors. Ascorbate, in particular, can be present in high concentrations in blood samples of individuals undergoing certain kinds of cancer therapy or of those consuming very high levels of the dietary supplement Vitamin C.

Other features are contemplated as well. For example, the first and second electrical pulses can be of opposite polarities, which avoids "burn off" and other consequences at the working electrode for the primary pulse. While prior "burn off" techniques reduced "blank current" problems, they can result in partially oxidizing (or reducing) the analyte to be measured, thereby reducing the signal-to-noise ratio of the sensor.

In other embodiments, a third potential (and accompanying electrical response measurement) can be applied using a low amplitude (rms) AC excitation, most conveniently between the first and second pulses of electrical excitation. This AC excitation allows for other compensations as has been described in U.S. Pat. Nos. 6,645,368; 7,407,811; 7,390,667 and 7,494,816. Exemplary compensation techniques have been implemented in state-of-the-art measurement methods as employed in, for example, the ACCU-CHEK® AVIVA® Meter and Strip System.

In other embodiments, and as will be explained in greater detail below, when the redox potential of the species responsible for the background and/or blank current is higher than the potential of the species responsible for the analyte signal, the first pulse's voltage magnitude in one embodiment is set to be higher than the second pulse's voltage magnitude. This helps to amplify the background and/or blank current signal in the first pulse, which can be used to compensate for background and/or blank current interference in the response to the second pulse.

It will be understood by one of skill in the art that a typical electrical potential for generating a current response has an amplitude (or magnitude) sufficiently high to drive a faradaic current response in a sample cell. Low amplitude AC excitation is employed to avoid driving a faradaic response while gleaning other information from the sample cell's electrical response to the AC excitation. Often, a high amplitude electrical potential is referred to as a DC signal, and the response to such a signal is referred to as a DC response. Nevertheless, application of a DC signal may be configured as a step-applied potential signal or may have some slight time-varying characteristics. Furthermore, application of a first DC signal followed by a second DC signal may be construed by one of skill in the art as application of a type of time-varied electrical potential, or an atypical AC signal of high amplitude, particularly when such pulses are provided according to a set pattern (i.e., first and second pulse applications repeated at least once). According to some embodiments, consideration should typically be given to the magnitude of the signal driving the response of the sample cell, and thus time varying aspects are generally the response of the sample cell, and the time varying aspects are generally secondary considerations. That said, it may be conventional still to refer to signals in this disclosure as "AC" or "DC," in which case it is primarily the magnitude of the signal that is being referred to as well as the type and purpose of electrical response being measured.

In one embodiment, the measurement method described herein overcomes the above-listed issues with glucose-specific enzymes, usually mutations of wild type enzymes, that are slow and variable in reaction velocity while maintaining a short overall test time, for example, between about 6 and 10 seconds. The method also overcomes the problems of measuring glucose concentration in the presence of substances that give rise to blank current, whether derived from the blood sample, the biosensor reagent or elsewhere (e.g., an electrochemically active impurity that may be present in any material used for the construction of the biosensor, and which can react with the mediator or the electrode). The combination of using an enzyme with high specificity and this measurement method provides for a sensor that is both maltose- and blood oxygen-insensitive. This allows analyte concentration to be accurately determined by individuals having high levels of maltose in their blood and in settings such as hospitals, where blood is drawn from various areas of the body that frequently have different blood oxygen levels.

Although the disclosure may refer alternately to the AC signal response of the sample cell as impedance or admittance (magnitude and/or phase), resistance, conductivity, current or charge and refer to the electrical excitation pulse responses as current, charge, resistance or conductivity, one of skill in the art will recognize that these measures are generally interchangeable. In other words, it is only necessary to adjust the measurement and correction mathematics to account for which measure is being employed.

Figure 4:
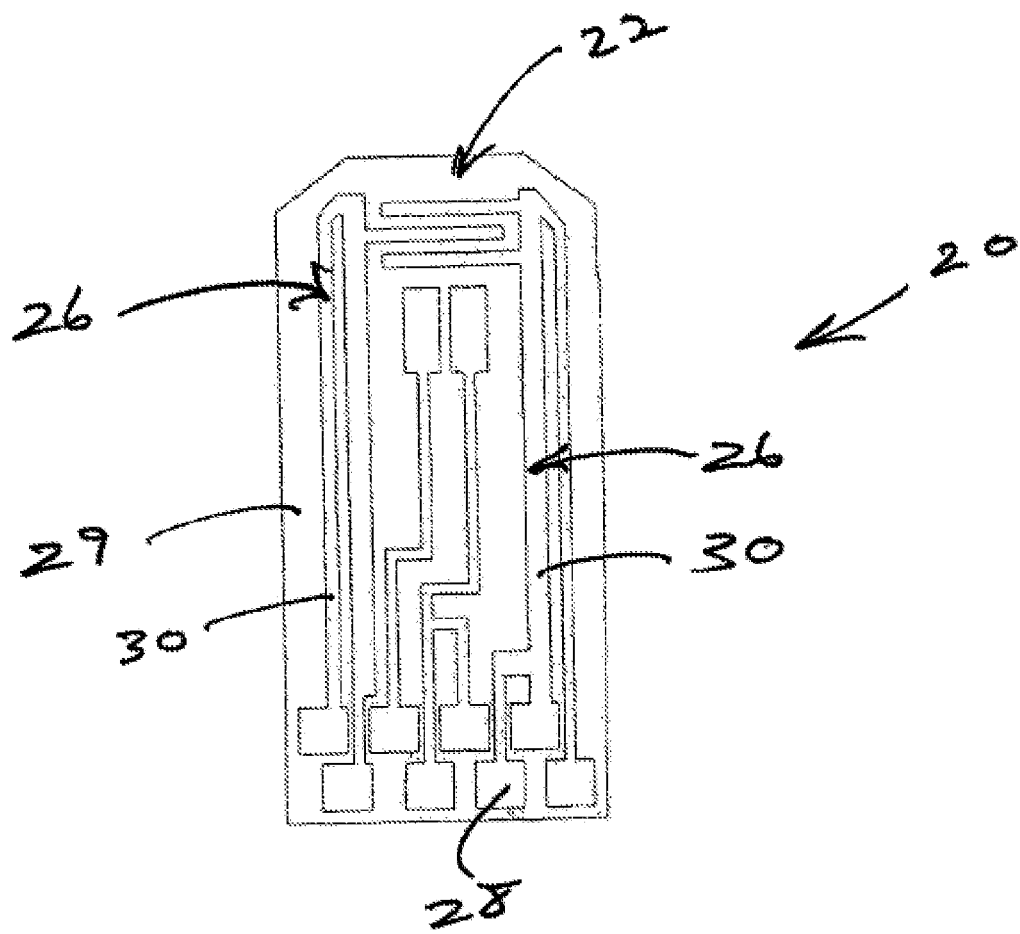
FIG. 4 is a first top view of a test strip with cover layers of the test strip removed.
Figure 5:
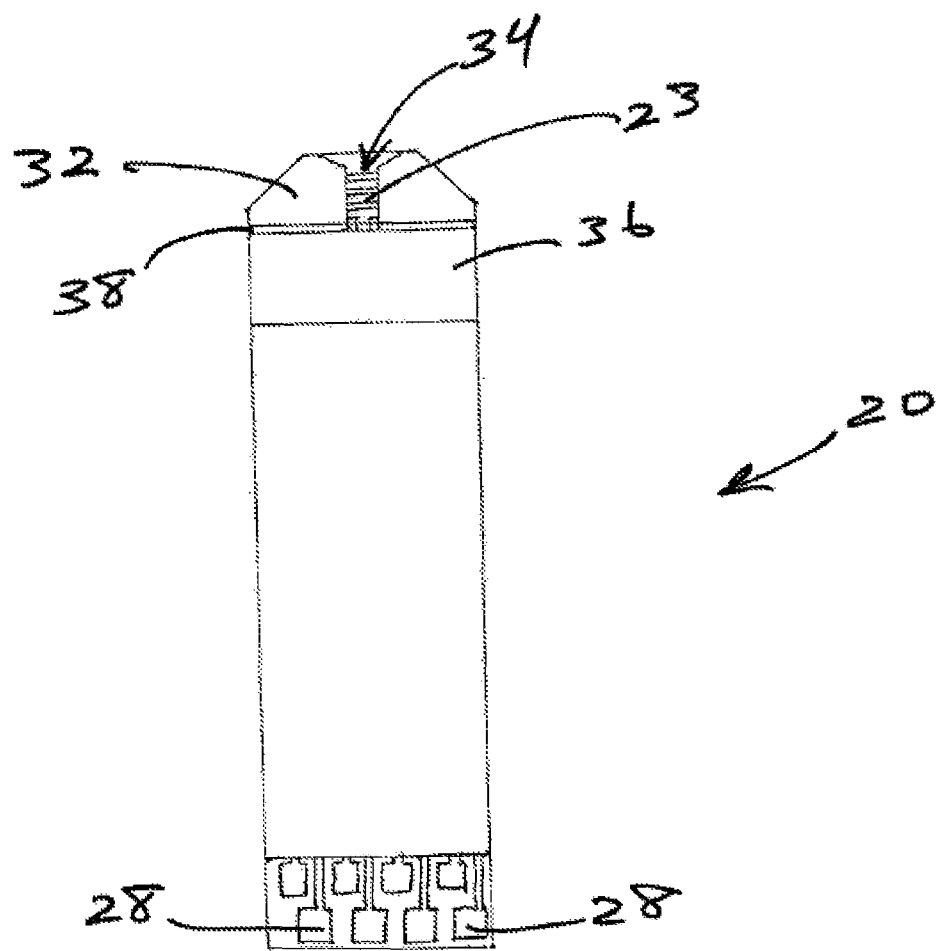
FIG. 5 is a second top view of the FIG. 4 test strip with the cover layers in place.

An example of an electrochemical analyte sensor 20, in particular an amperometric sensor, that can be used in conjunction with the techniques described herein, will be discussed with reference to FIGS. 4 and 5. It should be recognized that the sensor 20 in FIGS. 4 and 5 is merely an example of a type of sensor that can be used in conjunction with the methods described herein and that other types of sensors with different configurations can be used as well. For example, although the illustrated embodiment shows electrodes formed in an interdigitating array, the electrodes in other embodiments may not have an interdigitating construction or may include additional electrodes. As another example, the electrodes 22 in the illustrated embodiment have a co-planar configuration, but it should be appreciated that the electrodes 22 in other embodiments can have other configurations, such as a facing construction. For the sake of brevity as well as clarity, not all of the features of the sensor system will be described in detail below, but reference is made to U.S. Pat. Nos. 6,270,637 and 7,727,467.

Turning to FIG. 4, the sensor 20 includes an interdigitated array of electrodes 22 and a reagent layer 23 disposed on flexible substrate 29. One of the electrodes in the array 22 acts as a working electrode, and the other acts as a counter electrode. However, as alluded to before, the electrodes in accordance with one embodiment can switch roles. That is, an electrode in electrode array 22 may act at one time as a working electrode and may act at another time as a counter electrode. In the illustrated embodiment, two electrodes are shown, but it should be recognized that the sensor 20 in other embodiments can include more electrodes. The electrodes in electrode array 22 are connected to electrically-conductive connectors 26 that include contact pads 28 located on the surface of the flexible substrate 29, where the contact pads 28 are available to be contacted to an external electronic circuit such as a meter. The connectors 26 also include connector portions 30, which connect electrode elements at the array 22 to the pads 28, and which may typically be covered by an insulating layer.

Referring to FIG. 5, non-conductive spacer layer 32 (visible through a transparent foil) is disposed over the substrate 29 and connector portions 30 of the connectors 26. The spacer 32 defines a capillary sample chamber 34, and the sample chamber 34 has an inlet opening in which the fluid sample is drawn into the chamber 34. A reagent layer 23 is disposed over the array 22 within the sample chamber 34. The reagent layer 23 can include a mediator and enzymes that are selected to analyze the fluid sample. Foil 36 covers the spacer 32 and a portion of capillary chamber 34, except for an air vent 38, which is used to vent air from the chamber 34.

Figure 6:
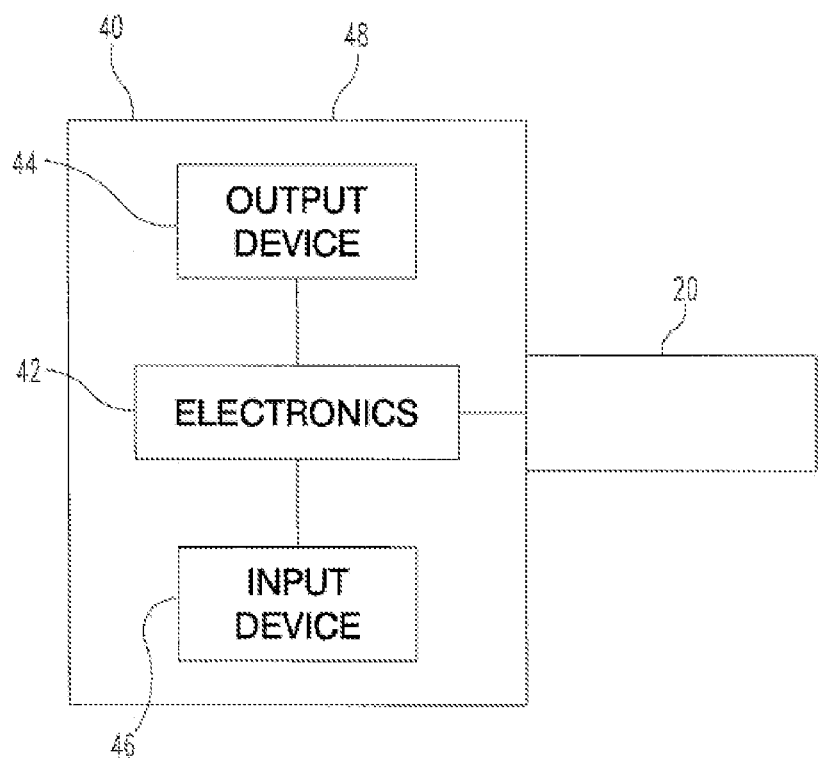
FIG. 6 is a block diagram of a meter system that uses the FIG. 4 test strip.

FIG. 6 is a block diagram providing an example of a meter 40, such as a portable blood glucose meter, to which the sensor 20 is operatively coupled during analysis. As should be appreciated, other types of instrumentation, besides the meter 40, can be used for analysis in other embodiments. In one embodiment, the test meter 40 applies a series of DC signals to the electrodes 22, and optionally AC signals, to obtain various responses from the sample being interrogated or analyzed. As shown, the meter 40 includes electronics 42, such as a clock, processor, calibration chip, memory and the like, which are used to analyze the fluid sample utilizing the techniques described herein. In the illustrated embodiment, the meter 40 includes output device 44, such as a display, speaker, wireless connection and/or printer that provides the results of the analysis as well as other information. The meter 40 also can include an input device 46, like an input button, keyboard, touch screen, port and/or microphone, in which the user can enter information into the meter 40 and/or control the operation of the meter 40. These various components of the meter 40 are housed in or on a meter housing 48.

It is contemplated that the meter 40 can include more or less components than are shown in the drawings. For example, the meter 40 in other forms can include a communication device that allows the meter to communicate directly or remotely with a computer or other types of devices. Moreover, as will be appreciated from the discussion below, other types of meters or instruments can be configured to analyze fluid samples using the techniques described herein. In addition, although the meter 40 is shown as being used in conjunction with just a test strip sensor 20, it should be understood that the meter 40 and test strip 20 can be incorporated into other types of devices, such as an integrated device. As an illustration, the multiple DC pulse analysis technique described herein can be used in conjunction with an integrated disposable, such as a Lancet Integrated Test (LIT) element or micro-sampler, in which the sensor 20 is attached to a lancet or other piercing means. See, e.g., U.S. Pat. Nos. 7,374,546 and 7,351,213.

Methods

Figure 7:
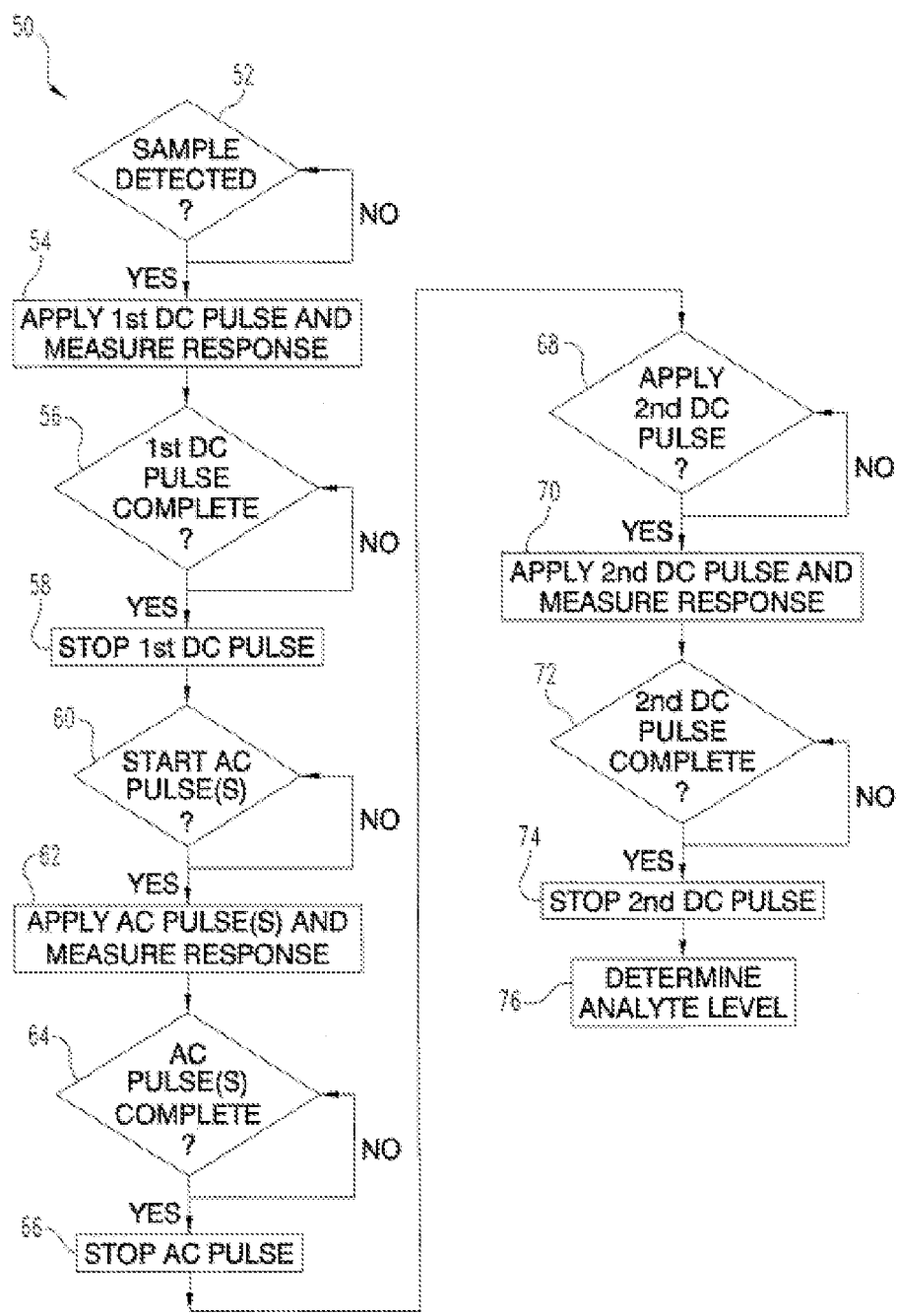
FIG. 7 is a flow diagram illustrating a measurement technique according to one embodiment as described herein.

An analysis method according to one embodiment can be initially described with reference to a flowchart 50 in FIG. 7, which illustrates the various stages of this technique. Note that the logic illustrated by the flowchart 50 in FIG. 7 is shown to help in the explanation of the method, and, in a practical application, the actual logic used may be different. For instance, it should be recognized that unless specified otherwise, the order of these stages can be different in other embodiments. As an example, some stages may occur simultaneously or in a different order than is shown.

With reference to FIGS. 6 and 7, when the test is initiated, the meter 40 via the sensor 20 detects the sample fill sufficiency in the sensor 20 in stage 52. As should be recognized, fill detection can be determined via various techniques as would occur to one of skill in the art, such as via separate or integral fill detection electrodes. Examples of some fill detection techniques are described in U.S. Pat. No. 7,407,811. The meter 40 continues to monitor for the sample fill sufficiency of the sensor in stage 52 until the fluid sample is detected in the sensor 20.

After detecting the fluid sample, the meter 40 applies a first DC signal or pulse to the electrodes 22 that has a first potential and polarity. It is contemplated that the first DC pulse of stage 54 can be applied as soon as the sample is detected in stage 52, that is, with no incubation time, or the first DC pulse can be applied after a specified wait time has elapsed, that is, after an incubation time.

While the first DC pulse is applied to the electrodes 22, the meter 40 detects the DC response from the sensor 20, such as the current. During stage 54, the meter 40 can measure the DC response one or more times. For example, the meter in one embodiment measures the DC response four times while the first DC pulse is applied, but it should be understood that the meter 40 can take more or fewer measurements during the first DC pulse. From these measurements, the meter 40 is capable of determining various parameters of the reaction, for example, the shape and/or time-to-current maximum of the current response to the first DC pulse, and the instantaneous rate of reaction (or degree of reaction completeness for a specified period) based on the shape and/or time-to-current maximum of the current response to the first DC pulse.

As should be recognized, the meter 40 can determine the appropriate compensation from the current response to the first DC pulse at any time. For example, the meter 40 can determine the appropriate compensation while the first DC pulse is applied, sometime afterwards, before the second DC pulse is applied, while the second DC pulse is applied, or sometime after the second DC pulse is applied.

In other embodiments, the compensated analyte measurement can be calculated without a discrete determination of a correction factor or compensation value to be applied to a separate analyte measurement. That is, while discrete current response measurements may be made from the application of the first DC pulse, those measurements may be included with current response measurements made from application of the second DC pulse (discussed below) in an algorithm adapted to compile all of the current response measurements to determine a compensated (e.g., weighted) effective current response value that is used to determine the estimated analyte value (such as blood glucose concentration). An exemplary algorithm is discussed below.

As should be recognized, no power supply (or battery) is able to supply a voltage or current that is perfectly constant over time, and therefore, it is contemplated that the DC signals or pulses according to the various methods described herein may have minor variations in their signals that should be determined to be within acceptable limits.

In the embodiment presently being discussed, the test has a fixed overall test time, and in one particular example, the first DC pulse is applied for a fixed period of time, such as for about 4 seconds after the sample is detected. Returning to the present fixed test time embodiment, the meter 40 in stage 56 (FIG. 7) continues to apply the first DC pulse and take measurements until the appropriate time has elapsed, and subsequently, the meter 40 in stage 58 stops applying the first DC pulse. When the first DC pulse stops, the potential applied to the electrodes 22 can become zero volts (0 V) (or thereabouts) by disruption of the circuit or by actively holding the applied potential at zero volts (either instance referred to herein as an "open cell condition"), or the applied potential may be held at some potential that is different than the one applied during the first DC pulse. For instance, the meter 40 in another embodiment applies the second DC pulse to the sensor 20 immediately after the first DC pulse stops, and in this particular example, the two pulses are differentiated by differences in polarity and/or magnitude.

Once the first DC pulse ceases, a delay (stage 60) can occur between when the first DC pulse stops and the second DC pulse starts, or there is no delay between the DC pulses. Optionally, one or more AC signals or pulses can be applied between the first and second DC pulses. It should be appreciated that in other embodiments the AC signal(s) may not be applied. Although FIG. 7 shows AC signals being applied between the first and second DC pulses, it is contemplated that the AC signals can be applied before the first DC signal is applied, at the same time the first DC pulse is applied, at the same time the second DC pulse is applied, across both DC pulses, and/or even after the second DC pulse stops, to name a few examples. As explained extensively in U.S. Pat. No. 7,407,811, the one or more AC signals can be used to correct many factors that can interfere with accurate readings, such as compensating for interferents in the sample, compensating for temperature of the sample, and/or correcting for differences in hematocrit levels.

Because the contribution of various factors to the impedance of a blood or other body fluid sample is a function of the applied signal, the effects of confounding factors (i.e., those other than the factors sought to be measured) can be substantially reduced by measuring the impedance of the blood sample in response to multiple signals. In particular, the effects of confounding factors (primarily temperature and hematocrit, but also including chemical interferents such as oxygen) contribute primarily to the resistivity of the sample, while the glucose-dependent reaction contributes primarily to the capacitance. Thus, the effects of the confounding factors can be eliminated by measuring the impedance of the blood sample to an AC excitation, either alone or in combination with a DC excitation. The impedance (or the impedance derived from admittance and phase information) of the AC signal is then used to correct the second DC signal.

It should be recognized that measurements at sufficiently high AC frequencies are relatively insensitive to the capacitive component of the sample's impedance, while low frequency (including DC) measurements are increasingly (with decreasing frequency) sensitive to both the resistive and the capacitive components of the sample's impedance. The resistive and capacitive components of the impedance can be better isolated by measuring the impedance at a larger number of frequencies. However, the cost and complexity of the meter increases as the number of measurements increases and the number of frequencies that need to be generated increases.

The AC signal applied in stage 62 has at least one portion that has an alternating potential or voltage. For example, the signal may be an "AC signal" having 100% alternating potential (voltage) and no DC portions; the signal may have AC and DC portions separated in time; or the signal may be AC with a DC offset (AC and DC signals superimposed). It is envisioned that various waveforms may be used in an AC signal, including, for example, sinusoidal, trapezoidal, triangular, square and filtered square. In one embodiment, the AC signal has a filtered square waveform that approximates a sine wave. This waveform can be generated more economically than a true sine wave, using a square wave generator and one or more filters.

During stage 62 (FIG. 7), the meter 40 in one embodiment generates AC signals at four frequencies and measures the AC response at each frequency. However, it is contemplated that more or less frequencies can be generated and corresponding responses measured at this stage. The response can be measured as current or voltage (preferably both magnitude and phase), and the impedance and/or admittance can be calculated therefrom. After the AC signal has been applied to the sample in the sensor for a specific time period and the response has been measured, the meter 40 steps up or down to the next frequency by some increment. In one embodiment, the generated frequencies are 1, 2, 10 and 20 kilohertz (kHz). One of skill in the art will appreciate that these values may be different in other embodiments. Although the AC signals have been described for being applied for the same specific fixed periods, it is contemplated that the AC signals in other embodiments can have different periods of time. Once the last AC signal has been applied and the AC response measured in stage 64, the meter 40 in stage 66 stops applying the AC signals to the sample in the sensor 20.

The second DC pulse is used primarily to analyze and measure the analyte concentration in the body fluid sample. In stage 68, the meter 40 may wait before applying the second DC (analysis) pulse in stage 70. Alternatively, there may be no delay before the second DC pulse is applied. As mentioned before, the second DC pulse in other embodiments can be applied right after the first DC pulse stops (at stage 58). Alternatively, or additionally, the second DC pulse and the AC signals in further embodiments can be applied at the same time. While the second DC pulse is applied to the sample in the sensor 20, the meter 40 measures the DC response one or more times. In one particular example, the DC response is measured four times at even intervals, but it is contemplated that more or less response measurements can be made and/or the measurements can be made at varying intervals.

The voltage of the second DC pulse applied in stage 70 can be the same as or different from the voltage of the first DC pulse in polarity and/or magnitude as long as the absolute magnitude is sufficiently large that the sources of the blank current and/or the sources of the glucose-related current (i.e., reduced mediator) are oxidized by one or the other of the electrodes during the application of both pulses. In one embodiment, the polarity of the second DC pulse is the opposite from the first DC pulse.

In the case where the polarities are reversed, the sensor 20 acts like a biamperometric sensor during both pulses because the composition of matter of the working electrode and the counter electrode are generally the same if not identical at both polarities. The roles of the electrodes 22 reverse when the second DC pulse is applied, such that the electrode that acted as the working electrode during the first DC pulse becomes the counter electrode when the second DC pulse is applied, and the counter electrode during the first DC pulse acts as a working electrode during the second DC pulse. This dual biamperometric arrangement typically can be used so long as the reagent is generally homogenous across both electrodes 22. On the other hand, if the reagent layer over the electrodes is not similar (e.g., thickness and/or composition is different), but the differences are consistent, it is contemplated that a correction factor can be used to compensate for these differences in the reagent over the electrodes 22. With the polarities of both DC pulses being different, two different physical electrodes 22 are used to make separate measurements with minimal interaction between the two measurements.

In the case where the first and second DC pulses share a common polarity, the measurements from the two pulses will not be entirely independent from one another because the first DC pulse will deplete the reduced mediator concentration over the same electrode prior to the second DC pulse. In other words, maintaining common polarities between the DC pulses may result in at least some depletion of the reduced mediator, such as phenylenediamine, close to the working electrode (anode) during the second DC pulse.

In embodiments in which polarities are reversed, the signal magnitude of the reduced mediator determination during the second DC pulse may be enhanced to the extent that reversal of polarities avoids consuming or burning off the species responsible for background or blank current on the electrode that becomes the working electrode during the second DC pulse. As mentioned before, although burning off the species responsible for blank current reduces the effect of blank current, it also partially oxidizes (or reduces) the analyte to be measured, thereby reducing the signal-to-noise ratio of the sensor. In addition, such biamperometric sensors can be simpler to manufacture. For example, the biamperometric sensors do not require a true counter/reference electrode, such as a Ag/AgCl electrode.

In other embodiments, however, a biamperometric system can result when using first and second DC pulses of common polarity, if the sensor is provided with a counter electrode that has an effective area (i.e., area exposed to reagent and sample) that is at least about twice the area of the working electrode. For example, ACCU-CHEK® AVIVA® Test Strips and ACCU-CHEK® PERFORMA® Test Strips each have interdigitated working and counter electrodes, where the working electrode comprises a single prong located between two prongs of the counter electrode, each prong having approximately the same area being exposed to the sample chamber provided for holding the sample.

As noted before, the magnitude of the voltages or potentials of the first and second DC pulses can be generally the same or different. When the redox potential of the species responsible for the background and/or blank current is higher than the potential of the species responsible for analyte signal, the first pulse's voltage magnitude in one embodiment is set to be higher than the second pulse's voltage magnitude. This helps to amplify the background and/or blank current signal in the first DC pulse, which can be used to compensate for background and/or blank current interference in the response to the second DC pulse. For example, the absolute value of the potentials applied during the first and second DC pulses can be 600 and 450 mV, respectively, but in other variations, the potentials can of course be different. As discussed above in the Background section, vial abuse can be one source for creating blank current problems. It has been found that blank current induced by vial abuse, as well as from other sources, can be compensated for by using this approach of having the absolute potential of the first DC pulse being greater than the one for the second DC pulse. It has been discovered that this approach can be especially helpful when the reagent contains a nitrosoaniline as a mediator precursor; that is, nitrosoaniline is provided in the reagent layer and requires reaction with an analyte to produce the actual mediator species for the system. In other words, a reagent layer with nitrosoaniline utilizes a reaction product between nitrosoaniline and an analyte as the actual electron-shuttling mediator. Also particularly helpful in such reagent systems is that the first DC pulse generates a current response unrelated to the aforementioned "burn off" solution of the prior art. Because nitrosoaniline is a mediator precursor, there generally is no significant issue relating to mediator being reduced by environmental conditions prior to dosing with a sample fluid. Thus, the first DC pulse does not function to return a mediator species back to an oxidized state, but instead is useful to accomplish compensation for other confounding issues.

Referring again to FIG. 7, when the DC pulse is applied in stage 70, the meter 40 measures the response to the DC pulse one or more times. In one embodiment, the meter 40 measures the response four times at evenly spaced intervals, but it should be appreciated that fewer or more measurements can be made at different intervals. It is further contemplated that in other embodiments the number of measurements and intervals between measurements made during the second DC pulse can be based on the results from the first DC pulse. For example, if it is determined from the first DC pulse that the reaction rate is fast, the intervals between measurements during the second DC pulse can be shortened and/or fewer measurements can be taken.

As noted before, the total time the second DC pulse is applied and the response measured in one embodiment can be fixed, but in other embodiments, the total test time can be variable, depending on the reaction rate detected during the first DC pulse. The meter 40 continues to apply the second DC pulse and take measurements in stage 72 until the predetermined or variable application time is complete for the second DC pulse. Once the time has elapsed, the second DC pulse is stopped in stage 74.

In one embodiment, the analyte level, such as blood glucose concentration, is determined after the second DC pulse is finished. It is contemplated that in other embodiments the analyte level can be determined while the second DC pulse is still being applied. During the analysis stage 76, the compensation for differences in reaction times and/or blank current can be achieved through a variety of techniques, such as regression and principal component analysis. In one approach, the meter 40 can utilize a calibration chip that stores information for various calibration curves and/or coefficients that vary depending on reaction times as well as other factors, which are then used to adjust the response for the second DC pulse. For example, based on the shape and time-to-maximum current for the response to the first DC pulse, the meter 40 can select corresponding calibration coefficients that appropriately adjust the results from the response to the second DC pulse.

According to one embodiment, a mathematical approach for estimating glucose and compensating for the effects of reaction velocity, electrochemical interferents (blank current), hematocrit and temperature, can be generally described with the following equation:

$$bG_{EST} = A + \text{Const} \times I_{eff} + \exp(f_{n1}(P_{eff}, Y_{eff}) \times (I_{eff})^{f_{n2}(P_{eff}, Y_{eff})})$$

where:

$bG_{EST}$=blood glucose estimate;
A=intercept;
Const=constant;
$I_{eff}$=weighted linear combination of discrete measurements of current during the two (or more) DC blocks;
$P_{eff}$=weighted linear combination of the discrete measurements of Phase angle;

$Y_{eff}$=weighted linear combination of the discrete measurements of Admittance; and $f_{n1}$ and $f_{n2}$=weighted linear combinations of $P_{eff}$ and $Y_{eff}$.

In one example, $I_{eff}$ is calculated using eight discrete measurements, four from the first DC excitation pulse and four from the second DC excitation pulse. In this same example, $Y_{eff}$ is calculated based on a weighted linear combination of four discrete measurements of Admittance during the AC excitation phase, and $P_{eff}$ is calculated based on a weighted linear combination of four discrete measurements of Phase angle during the AC excitation phase. As should be appreciated, more or less measurements of current, admittance and/or phase angle can be used in other embodiments. The best coefficients for all these linear terms can be calculated using non-linear regression techniques applied to covariate data gathered with blood samples of varying glucose, hematocrit and temperature in a manner familiar to one of skill in the art. In another embodiment, the coefficients, which represent a calibration code for the measurement algorithm, are determined using a grid search algorithm in accordance with calculated optimization criteria. Again, such a technique is familiar to one of skill in the art. Thus, the slope and power terms of $I_{eff}$ above are able to provide the necessary compensation for the influence of these covariates on the dose response slope and curvature.

EXAMPLES

The invention will be more fully understood upon consideration of the following non-limiting examples, which are offered for purposes of illustration, not limitation. In a particular exemplary embodiment, the calibration code can be determined for blood samples using an ACCU-CHEK® PERFORMA® Test Strip.

Example 1

Figure 8:
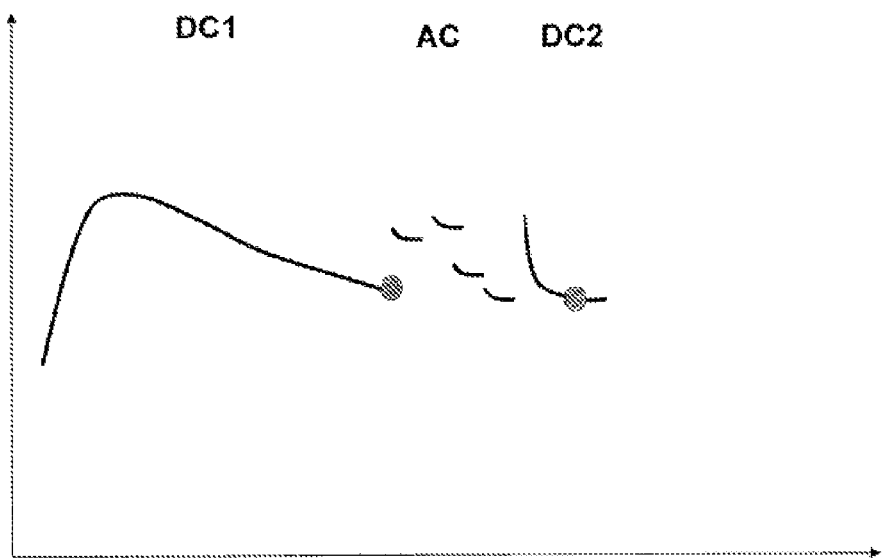
FIG. 8 is a graph that represents an example of various signals applied to a fluid sample in an electrochemical cell and corresponding responses utilizing a fixed test time sequence technique according to one embodiment as described herein.

A test sequence is employed comprising a first DC test block followed by 4 AC test blocks with different excitation frequencies, followed by a second DC test block. Shown in FIG. 8 are representative current responses for this system, with the horizontal axis representing time after fill sufficiency and the vertical axis on the left representing DC voltage. A second vertical axis, corresponding to the four AC responses, represents the frequencies of the four AC test blocks. From each of the DC test blocks, four DC readings are taken at different time points, and from each of the AC test blocks a phase-shift and an admittance value are determined and used for the glucose calculation algorithm. In total, 8 AC observables and 8 DC observables are used.

From the four phase-shift values, a weighted combination P-Effective is calculated: $P_{eff}=(p1*P1)+(p2*P2)+(p3*P3)+(p4*P4)$.

From the four admittance values, a weighted combination Y-Effective is calculated: $Y_{eff}=(y1*Y1)+(y2*Y2)+(y3*Y3)+(y4*Y4)$.

From the eight DC readings, a weighted combination I-Effective is calculated: $I_{eff}=(i1*I1)+(i2*I2)+(i3*I3)+(i4*I4)+(i5*I5)+(i6*I6)+(i7*I7)+(i7*I7)$.

Using the effective values, a glucose concentration is calculated using the following equation: Est gluc=a+(b+exp$(b0+P_{eff}+Y_{eff}))*I_{eff}{}^{\wedge}(c0+c1*P_{eff}+c2*Y_{eff})$.

So in total, 22 coefficients p1, p2, p3, p4, y1, y2, y3, y4, i1, i2, i3, i4, i5, i6, i7, i8, a, b, b0, c0, c1 and c2 define the calibration code.

The coefficients represent the calibration code for a given blood glucose measuring system. The method on how to find suitable values for all coefficients is in principle a kind of grid search algorithm. Therefore, at first, an optimization criterion has to be defined.

The optimization criterion is calculated as a weighted sum of characteristic statistical values describing the requirements for the accuracy, trueness and precision of the glucose measurement. Those calculated values to calculate the single optimization criterion are:

1. The sum "A" of all biases of a calculated glucose result versus the chosen glucose reference value outside certain given limits. Reference glucose concentrations below 75 mg/dL are calculated as absolute biases, and values above 75 mg/dL are calculated as relative biases. For the example, the limits above are set to +/−9 mg/dL below 75 mg/dL and 12% above 75 mg/dL.
2. The sum "B" of all mean biases of measurements between a control condition and a test condition outside of certain limits. Here, the mean biases are calculated from single measurements (e.g., n=8) for the same sample and test condition. The limits are set to +/−10 mg/dL or +/−10%. Different test and control conditions are used for the training dataset listed below.
3. The averaged precisions "C" of all individual measurements tested for all samples and test conditions.
4. The linearity "D" of the pooled measurements over the glucose range for all control conditions (measurements at room temperature and normal hematocrits without adding interfering substances with strips used fresh from the primary packing).

The optimization criterion (OC) is calculated as OC=a*A+b*B+c*C+d*D, where a, b, c, and d are the weighting coefficients. As the value for OC gets smaller, the better the defined test requirements are fulfilled. The weighting coefficients have to be chosen such that all defined criteria are met as best as possible for a given time frame (grid search run time).

To create a suitable training data set for the basic calibration, all relevant types of sample material at all relevant conditions have to be measured with the selected test sequence. In parallel for all tested samples, a reference glucose value must be determined by a suitable reference method. For the example described here, the hexokinase method on a Hitachi analyzer testing the glucose concentration in the plasma phase of the samples was used, so the estimated glucose results are referenced to the plasma concentrations.

As a training data set, the following sample material and test conditions were measured:

1. Manipulated venous blood samples adjusted to different hematocrit and glucose levels were tested at different ambient temperatures.
2. Manipulated venous blood samples adjusted to different hematocrit and glucose levels spiked with different concentrations of ascorbic acid were tested at different ambient temperatures.
3. Manipulated venous blood samples adjusted to different hematocrit and glucose levels were tested at different ambient temperatures using test strips exposed to warm and humid conditions for different stressing times before testing. Strips were re-dried before testing.
4. Manipulated venous blood samples adjusted to different hematocrit and glucose levels were tested at different ambient temperatures using test strips stored in the primary packing for different storage times. The test strips were stored at 45° C. to accelerate possible rotting effects.

5. Manipulated venous blood samples adjusted to different hematocrit and glucose levels were tested with the samples at room temperature and samples heated up to 37° C. Measurements were performed at different ambient temperatures.
6. As a model of non-glucose specific reactions of the enzyme with other sugars that may occur in patient blood samples, blood samples spiked with those sugars at different concentration levels were tested again in combination with different hematocrit and glucose levels tested at different ambient temperatures.

In total for the example, more than 600 combinations were used to create the training dataset that was measured. For each test combination, eight (8) test strips were measured, so for each combination an SD or CV value can be calculated.

For the code-finding algorithm, a data table with a row for each individual measurement, and columns containing all observables defined by the test sequence and the corresponding reference glucose values is generated. Additionally, a column containing a weighting factor is part of the data table. This weighting factor will be subsequently used to weight the individual biases differently when calculating the optimization criteria. This allows focusing the optimization process to selected test combinations and optimizing the code with respect to different bias limits.

As a second dataset, all mean values for each test combination and each observable are calculated. Each row now contains the data for each test combination and the corresponding control condition with the related reference values. Examples for control and test conditions here are a sample at a normal hematocrit level tested at room temperature as control condition compared to samples at non normal hematocrits tested at temperatures other than room temperature. Other pairs are biases between fresh test strips versus stressed test strips, cold versus warm samples or samples spiked with interfering constituents versus unspiked samples.

In a next step, start values for all coefficients of the code need to be defined. For the examples, the coefficients are set to the following start values: i8=1; c0=1; all other coefficients are set to zero.

Using these start-values for the coefficients, for each measurement an estimated glucose concentration is calculated and then all individual biases versus the reference glucoses are calculated. Below a reference concentration of 75 mg/dL, the bias NE (normalized error) is calculated as an absolute value. Above 75 mg/dL, the bias NE is calculated as a relative value (est gluc−ref glu)/ref glu*100 in %.

From all the calculated biases, the OC is calculated. In a first round only, the biases of the individual measurements versus the reference glucose are used. The OC is calculated as: OCa=sum(clipLower(NEi, uta)−uta)−sum(clipUpper (NEi, lta)−lta.

In this equation "uta" and "lta" are defined as an upper and lower bias thresholds. "NEi" is the calculated bias for an individual measurement. OC here is the sum of all biases outside the defined thresholds. For the example, these thresholds are set to +20 and −20. To define those limits differently for different glucose ranges, the data weighting factor is used. If all biases below 75 mg/dL reference glucose outside +/9 mg/dL shall be minimized, the related biases are multiplied by 20/9. If above 75 mg/dL, the limits shall be +/12%, and the weighting factor is set to 20/12.

If OCa is calculated for the starting coefficients, the value is stored. Now a first coefficient is changed by a fixed step down, and OCa is calculated again. Then, the same coefficient is changed one step up, and OC again is calculated. Now the first coefficient is set back to the start value, and a second coefficient is changed. This is repeated for a selected set of coefficients at any step down-step up for all possible combinations. The best OCa of any iteration is then kept, and a new iteration is started from the best code for the selected coefficient set found in this round.

The iterations were not done with all 22 coefficients at the same time because this would result in too many combinations: $3^{22}$ steps.

Therefore, for the examples described here, groups of eight coefficients are used for every iteration resulting in $3^8$=6561 steps to be tested with all datasets (in the example 4242 datasets corresponding to all individual calibration measurements are used, which then results in 6515×4242 calculations).

From iteration to iteration, the combination of the selected eight coefficients is changing so that in a complete iteration round, all coefficients get changed. For the example, 12 combinations are used, selected by related observable groups and also randomized combinations updated for each iteration round.

For the first part of this localized grid search algorithm, fixed steps for the coefficient changes are used. The step sizes are set individually for each coefficient defined by a list of different factors. These factors are selected in a way that all coefficients are continuously changing from iteration to iteration. Therefore, the changing from iteration to iteration is monitored, and the step size factors are adjusted until all coefficients continuously vary with the ongoing improvement of the optimization criteria (value gets smaller). Overlaid to those factors, a general factor to adjust the step sizes from iteration round to iteration round is used to adjust the step size such that each round is delivering a further improved OC. If in a round no improvement is found, then the step size is reduced. If in a round a lower OC value is found, then the step size is increased by increasing the general factor. After a defined number of optimization rounds, the general factor is reset to its start value. As a result, the localized grid search pattern is oscillating.

The OC value is monitored over the time during which the searching algorithm is running. If the OC change rate falls below a defined value (a local minimum is found for a set of coefficients), the step size strategy gets changed. The step size now is calculated as a portion of the size of the coefficient itself. This is done by calculating a randomized step size in a range from +/− of the coefficient value individually for every coefficient. For each iteration step, this randomized step size is calculated anew. The individual step size factors and the common factor are used in the same way as they were used with the fixed step sizes.

If the OC value reaches a steady state, this represents a local minimum in the grid search ranges. As a result, biases greater than the defined limits should now be reduced to a minimum. Ideally, no biases are outside the limits. For the training data set used here, test sequence and glucose calculation for nearly 97 percent of the data points fall within limits of +/−9 mg/dL or +/−12%.

In a next step, the OC is extended to improve the biases between the control conditions and test conditions. As such, the second data table containing the sample mean values is used. The biases "avNEct" between all test conditions and control conditions are now additionally calculated for all changed coefficients in the grid search algorithm. "avNEct" is calculated as avNEct=averaged NE control condition− averaged NE test condition.

As part of the OC, OCb is calculated by the equation: OCb=sum(clipLower(avNEcti, utb)−utb)−sum(clipUpper (avNEcti, ltb)−ltb, where utb and ltb are the bias limits for the criterion OCb. In the example, the limits were set to +10 and −10.

The new OC now is OC=a*OCa+b*OCb, where a and b are weighting coefficients. These weighting coefficients have to be chosen such that both the OC individually can be found as best as possible within a given time frame. As a result, the first OC can be compromised by optimizing the second one to some degree.

Then, in a third step, the OC again are extended to optimize the within-sample precision. This precision is calculated using the first data table. For each tested coefficient set, the estimated glucose concentration is calculated as a mean value, and a SD value and a CV value for every test combination of the n=8 measurements are calculated. As the OC, OCc, all calculated SDs (below 75 mg/dL) or CVs (above 75 mg/dL) mean values are averaged: OCc=av (SDCVs). The new total OC is now calculated by: OC=a*OCa+b*OCb+c*OCc.

The best combination of weighting factors, taking into account also the different sizes of the OCi values, should be found in order to get the best overall result based on the defined acceptance criteria limits.

As a fourth part of the OC, the total system error (TSE) or root mean square differential (RMSD) or the precision ($r^2$ values) of a linear regression of a subset of the training dataset was used for the described example. As the subset, all data from measurements with normal samples over the glucose range (normal hematocrit, no interfering substances added) and fresh test strips tested at room temperature was selected. The reason for this criterion is to deliver a code, where the "normal" data is in good agreement with the reference method with a good accuracy and linearly across the glucose range.

To reduce the time to find a good code, each iteration round is stopped when a new best (i.e., lower OC) is found and restarted from the newly found set of coefficients.

If selected biases caused by special interferences have to be reduced further for those test combinations, an individual OC can be calculated and weighted in the total OC. This OC then needs to be calculated based on a corresponding subset of the training dataset. So for this example, for the biases resulting from testing cold versus warm samples, an OC using limits of +/−3 was used (or alternatively the RMSD value, as OC values for this data subset, was calculated for all tested codes).

Optionally, the RMSD values for the whole dataset can be calculated for all coefficient variations and used as an additional part of the OC.

Although the method has been described generally with reference to two DC pulses, it should be recognized that a different number of DC pulses can be used. For example, three DC pulses can be applied in another approach. In another example, no time elapses between the first and second DC pulses such that only a single pulse appears to be applied. With this example, some of the DC response measurement points are used to determine the analyte level, while other DC response points are used for reaction time/ blank current compensation.

Example 2

Figure 9:
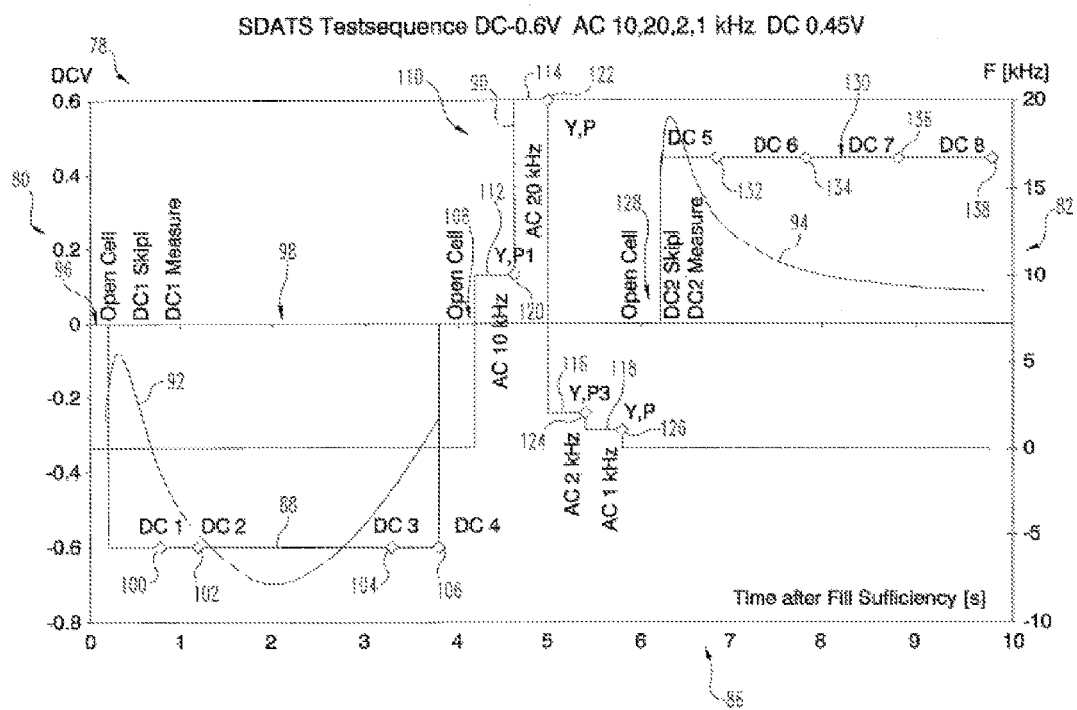
FIG. 9 is a graph that represents an example of various signals applied to a sample and corresponding responses utilizing a fixed test time sequence technique according to one embodiment as described herein.

FIG. 9 illustrates a specific embodiment in which the first pulse and second pulse are of opposite polarity, which can be particularly useful for compensating for various factors such as, for example, slow enzyme kinetics. FIG. 9 shows a graph 78 of an example of a fixed test time sequence in accordance with one embodiment. As can be seen, the graph 78 has a first y-axis 80 located on the left side of FIG. 9 that represents the DC voltage level (in volts), including polarity, as applied during the DC pulses. In other words, to determine the voltage and polarity of the applied DC pulses, reference should be made to the first y-axis 80. A second y-axis 82 shows the frequency levels (in kHz) applied during the AC pulses. In other words, to determine the frequency levels (in kHz) applied during the applied AC pulses, reference should be made to the second y-axis 82. Graph 78 also has an x-axis 86 that indicates the time (in seconds) after fill sufficiency of the sensor 20 is detected.

Graph 78 further includes a line 88 that represents the DC signal applied to the electrodes 22 by the meter 40 and a line 90 that represents the AC signal applied to the electrodes 22. Line 92 in the graph 78 represents the response curve to the first DC pulse 88, and line 94 represents the current response curve for the second DC pulse (no axis is given for the units of current).

With reference to FIGS. 7 and 9, when the sample is initially detected in stage 52 (time=0), there can be a delay in applying the first DC pulse. Portion 96 of DC signal line 88 represents the open cell condition that exists during this delay prior to the application of the first DC pulse. Portion 98 of the DC signal line 88 shows the first DC pulse block when the first DC pulse is applied. As can be seen, the first DC pulse 98 is −600 mV, but of course, other voltages can be applied in different embodiments. It should be noted that graph 78 in some ways shows an idealized version of the pulses when applied, and during practice, the shapes of the pulses may slightly vary. For example, the edges of the DC pulse might be rounded. When the first DC pulse 98 is applied, the first DC response 92 is generated, and the first DC response 92 is measured a number of times as indicated by first DC measurement points 100 (DC 1), 102 (DC 2), 104 (DC 3) and 106 (DC 4). In the illustrated embodiment, four measurements are taken during the first DC pulse 98, but again, it should be understood that more or less measurements at different intervals can be taken during the first DC pulse 98. The measured first DC response 92 is later used to compensate for a number of issues, such as reaction velocity variation and blank current, to name a few examples. For example, the first four DC response measurements can be used to determine the shape and/or time-to-maximum current of the response, which can be indicative of reaction velocity.

After a predetermined amount of time, which in the illustrated embodiment is somewhat less than 4 seconds after fill sufficiency was detected, the first DC pulse 98 is stopped (stage 58 in FIG. 7) so as to create an open cell condition 108 in which no voltage is applied to the electrodes 22. After a slight delay, a series of AC pulses 110 are applied to the sample (stage 60 in FIG. 4). As mentioned before, the AC pulses 110 may be optional for other embodiments. Referring to FIG. 9, first 112, second 114, third 116 and fourth 118 AC pulses of different frequencies are applied to the electrodes 22. In FIG. 9, the first 112, second 114, third 116 and fourth 118 AC pulses are at 10 kHz, 20 kHz, 2 kHz and 1 kHz, respectively. At the end of the first 112, second 114, third 116 and fourth 118 AC pulses, first 120, second 122, third 124 and fourth 126 AC response measurements are taken, respectively. As mentioned before, more or fewer AC pulses can be applied at different frequencies and/or sequences. The measured AC responses can be used later to correct for a number of factors, such as hematocrit levels.

An open cell condition 128 temporarily exists again after the last AC pulse has been applied and before the second DC pulse 130 is applied. Looking at FIG. 9, after about 6 seconds from the initial fill sufficiency detection, the second DC pulse is applied (stage 70 in FIG. 7) as is indicated by portion 130 of the DC signal line 88. In the illustrated embodiment, the second DC pulse 130 has a polarity that is opposite from the first DC pulse 98. To mention again, the reversal of the polarities between the first 98 and second 130 DC pulses does not deplete the concentration of the target analyte, such as glucose, at the electrode that eventually becomes the working electrode during the second DC pulse 130. This helps to enhance the quality of the analyte concentration determination during the second DC pulse 130. The reversal of polarities also avoids consuming or burning off the species responsible for the background or blank current on the electrode that becomes the working electrode during the second DC pulse 130 and which is typically used to determine analyte concentration.

The second DC pulse 130 in FIG. 9 is smaller in magnitude than the first DC pulse 98. Specifically, the potential applied during the second DC pulse 130 has a magnitude of 450 mV, as compared to the first DC pulse 98, which has a magnitude of 600 mV. Again, the applied voltages during each pulse can be different in other embodiments. Having the magnitude of the first DC pulse 98 higher than the second DC pulse 130 helps amplify the blank current signal in the first DC pulse 98, which can be used to compensate for blank current interference in the second DC response 94.

In FIG. 9, the second DC response 94 is measured at generally evenly spaced intervals as indicated by second DC measurement points 132 (DC 5), 134 (DC 6), 136 (DC 7) and 138 (DC 8), but in other embodiments, more or fewer measurements can be taken at varying intervals. The time between when the first DC pulse 98 ends and the second DC pulse 130 begins is 100 milliseconds (ms) in one embodiment. In other embodiments, the time between when the first DC pulse 98 ends and the second DC pulse 130 begins can be several seconds. In still other embodiments, the AC pulses 110 and corresponding measurements occur at the end of the test, after the second DC pulse 130. In the embodiment depicted in FIG. 9, the total test time is approximately less than 10 seconds, but the total test time and/or the timing of the various stages can differ in other embodiments. For example, there may be less than 1 ms or less than 1 microsecond (µs) between the DC pulses, and/or the AC pulses may be omitted entirely.

As discussed above, the first DC response 92 and the responses from the AC pulses 110 are used to correct the second DC response based on a number of factors. For instance, the first DC response 92 is used to compensate for varying degrees of completion in assay employing a fixed measurement time. To obtain a reading, such as the blood glucose value, the four readings from the first DC block 98 are mathematically combined together with the four readings from the second DC pulse 130, as well as the four readings from the AC pulses. The combination of these readings helps to compensate for slow reaction kinetics due to temperature extremes, hematocrit level variations, and/or slow enzymes. Further, the combination of readings helps to correct for blank (background) current that can result from aging or environmental exposure. The compensation for differences in reaction times and/or blank current can be achieved through a variety of techniques, such as regression and principal component analysis. The results from the analysis are then outputted via the output device of the meter 40.

Example 3

In an alternative embodiment, the test sequence illustrated in FIG. 9 is altered with regard to the duration of each DC and AC pulse, as well as the magnitudes of the DC pulses. For example, with reference to the sequence references of FIG. 9, the open cell condition 96 preceding the first DC pulse 98 lasts about 2 seconds, the first DC pulse 98 has a magnitude and polarity of about +450 mV and lasts about 2.5 seconds, open cell condition 108 lasts about a quarter of a second, AC signal 112 lasts about a half second at a frequency of about 10 kHz, AC signal 114 lasts about a quarter of a second at a frequency of about 20 kHz, AC signal 116 lasts about a quarter of a second at a frequency of about 2 kHz, AC signal 118 lasts about a quarter of a second at a frequency of about 1 kHz, open cell condition 128 lasts about a quarter of a second, and second DC pulse 130 has a magnitude and polarity of about +450 mV and lasts about 2.5 seconds.

Figure 10:
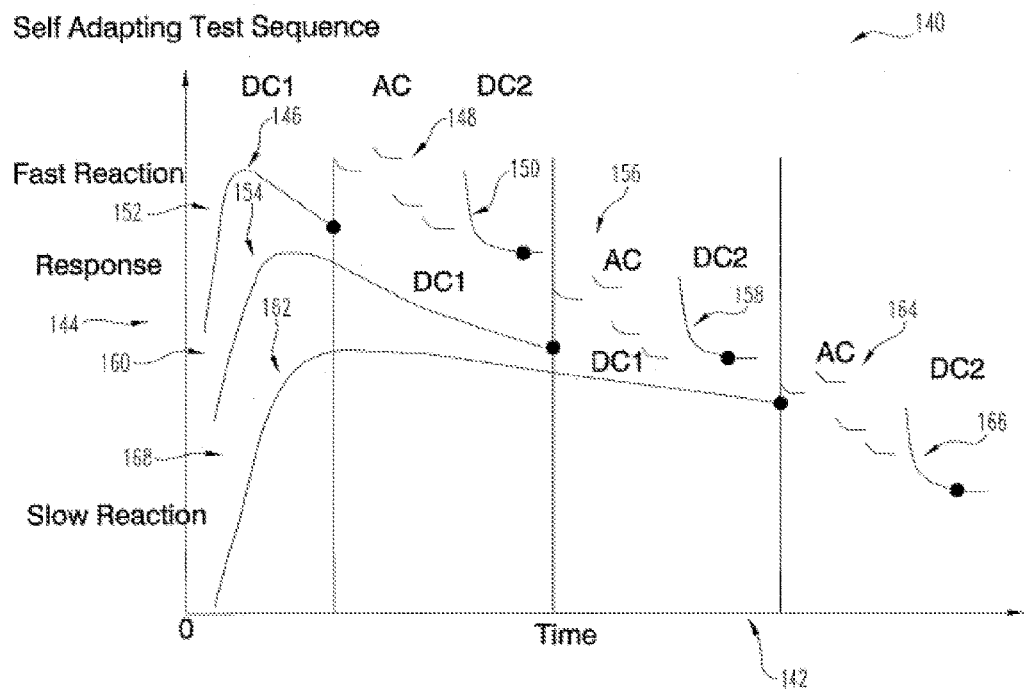
FIG. 10 is a graph illustrating the response curves for various reaction times utilizing a self-adapting test sequence according to one embodiment as described herein.

Certain embodiments have proven useful for determining a glucose concentration from blood samples compensated for electrochemically active interferents such as, for example, ascorbate. FIG. 10 shows a graph of calculated blood glucose in a normalized error format, obtained using a sequence similar to Example 1 and a production variety biosensor, namely the ACCU-CHEK® PERFORMA® Plus Test Strip comprising a mutant PQQ-GDH enzyme. The covariate study reported glucose concentrations in the presence of varying amounts of ascorbate that was added to the blood samples under test.

The data shows that the amount of interference from the addition of 30 mg/dL of ascorbate to a blood sample does not exceed about 12% of the reported glucose in a control sample containing no ascorbate, as calculated using this sequence. This maximum level of interference was observed in blood samples having between about 100 and about 200 mg/dL of actual glucose.

Figure 11:
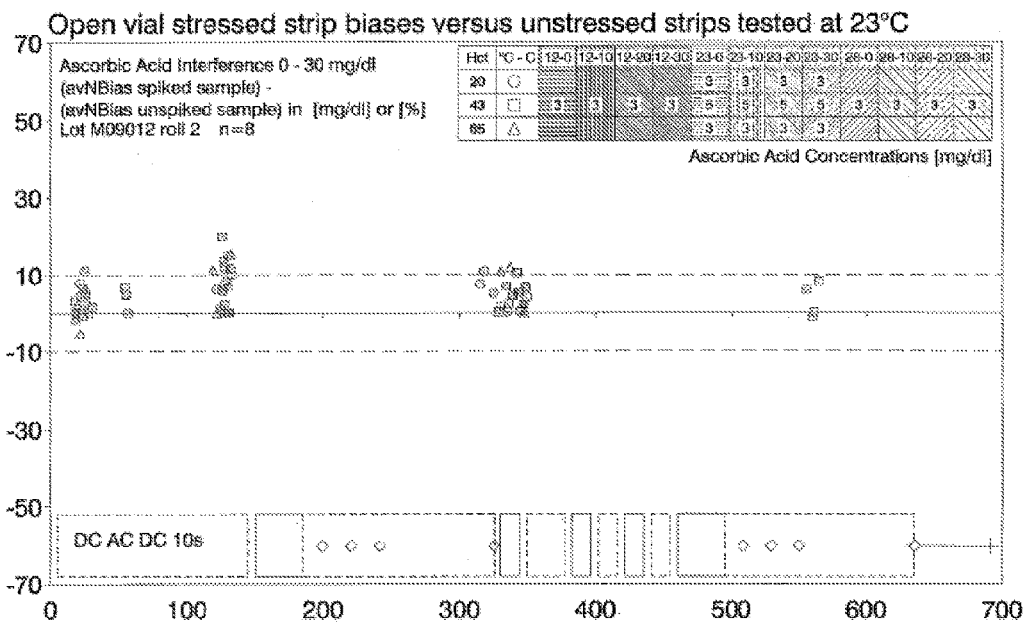
FIG. 11 is a graph illustrating calculated blood glucose in normalized error format for a covariate study of levels of ascorbate in blood using a test sequence according to one embodiment as described herein.
Figure 12:
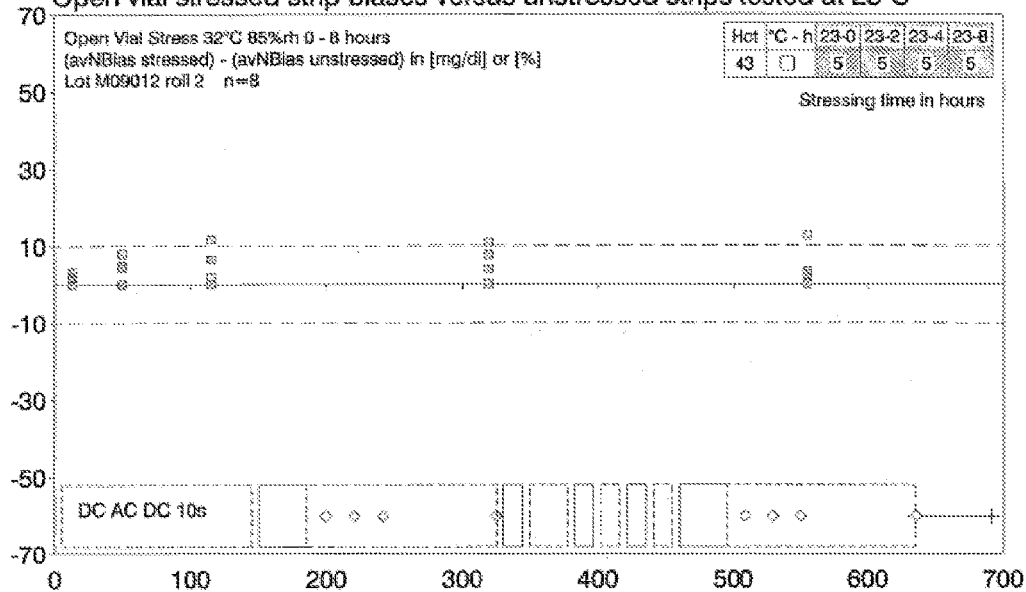
FIG. 12 is a graph illustrating calculated blood glucose in normalized error format for a covariate study using stressed strips (e.g., high temperature and humidity exposure) to test blood samples with various levels of glucose, using the same sequence according to the embodiment of FIG. 11.

FIG. 11 shows data from another covariate study involving stressed strips. The graph shows calculated blood glucose in normalized error format, obtained using the ACCU-CHEK® PERFORMA® Plus Test Strips and the test sequence from FIG. 10. The test strips were exposed to high temperature and humidity prior to testing blood samples of various glucose levels, indicated by the reference glucose axis (x-axis) of the graph. This exposure, which models what is typically referred to as open vial abuse of the test strips, causes decomposition of the mediator in the reagent layer, and formation of species giving rise to blank current as a source of error. The y-axis shows percentage of error of the reported glucose levels compared to actual levels. The data in FIG. 11 indicates that the amount of error from 8 hours of exposure does not exceed about 12% of the reported glucose derived from control strips that were not exposed to high temperature and humidity. This maximum level of error was observed in blood samples again having between about 100 and 200 mg/dL of actual glucose.

FIG. 10 is a graph 140 illustrating the response curves for various reaction times utilizing a self-adapting test sequence in accordance with another embodiment. With the self-adapting test sequence technique, the timing of the sequences varies depending on the reaction velocity detected during the first DC pulse. In the graph 140, the x-axis 142 corresponds to the time after fill sufficiency is detected in the sensor 20, and the y-axis 144 represents the response, such as the electrode current. The graph 140 in FIG. 10 depicts three types of reactions to the application of a potential that can occur during testing—a fast reaction 152, a medium length reaction 160, and a slow reaction 168. For a fast reaction, FIG. 10 shows a first DC pulse response 146 followed by four AC pulse responses 148, which are followed by a second DC pulse response 150. Depicted below the responses for a fast reaction 152 are responses for a medium length reaction 160, which include a first DC pulse response 154, followed by four AC pulse responses 156, followed by a second DC pulse response 158. Depicted below the responses for a medium length reaction 160 are responses for a slow reaction 168, which include a first DC pulse response 162, followed by four AC pulse responses 164, followed by a second DC pulse response 166.

Based on factors, such as the time-to-maximum current value, shape and/or slope of the response for the first DC pulse, the meter 40 is able to determine the reaction velocity. Depending on the detected reaction velocity, the meter 40 is able to shorten or lengthen the overall test time or the various testing stages. As an example, if the meter 40 detects a fast reaction 152 to the first DC pulse response 146, the duration of the first DC pulse can be shortened, and the AC and second DC pulses can be applied sooner. This in turn shortens the incubation time for the reaction over the electrode 22 that acts as the working electrode during the second DC pulse. In contrast, if the meter 40 detects that the response 162 to the first DC pulse is slow (reaction 168), the duration of the first DC pulse is lengthened such that the AC and second DC pulses are applied later. The later application of the second DC pulse increases the incubation time over the working electrode of the second DC pulse.

Although the duration of the AC and second DC pulses are depicted in FIG. 10 as being the same regardless of reaction time, it should be understood that in other embodiments the duration of the AC and second DC pulses can vary as well.

As discussed above, the measurement technique described herein overcomes several issues with glucose-specific enzymes, usually mutations of wild type enzymes that are slow and variable in reaction velocity. For example, it has been discovered that this technique is beneficial for sensors made with mutant PQQ-GDH enzymes or even mutant GOD enzymes. The combination of using an enzyme with high specificity and this measurement technique provides for a sensor that is both maltose and blood oxygen insensitive. This allows the analyte concentration to be accurately determined by patients who have high levels of maltose in their blood and in settings, such as hospitals, where blood is drawn from different areas of the body that have different blood oxygen levels.

As indicated above, sources of error relate not just to electroactive interferent species, blood component interferents, or enzyme reaction kinetics, but also to instances in which an enzyme, such as glucose oxidase, introduces an oxygenation level that will need correction in the determination of the concentration of the analyte being tested.

Example 4

A cell for receiving the blood sample is provided. The cell supports a chemistry that reacts with the blood sample. Further in the cell are first and second terminals across which the reaction of the blood sample can be analyzed. A test sample of the blood is provided to the cell. A further instrument is provided that has first and second terminals corresponding to the first and second terminals in the cell. The first and second terminals, respectively, of the instrument are placed such that they are in contact with the first and second terminals of the cell, respectively, and in a position to allow the instrument to analyze the reaction. Included in the instrument is a controller, which applies a voltage between the first and second terminals of the instrument. Two current responses from the applied voltage potential are measured, and these two current responses are used to determine the oxygenation level of the blood sample. In turn, once the oxygenation level of the blood sample is determined, the concentration of the glucose can be calculated.

The voltage potentials applied to the test sample include, in certain embodiments, a first potential applied at a first time and a second potential applied at a later second time. In one embodiment, the first potential and second potential have different absolute magnitudes. In other embodiments, the absolute magnitudes are substantially the same. The current response of the sample to the first applied potential is measured, and the current response of the sample to the second applied potential is measured, resulting in a first response and a second response. The sensitivities of the current responses to glucose for the first and second responses have been found to co-vary in a fixed proportion that is governed by the system diffusion, while the offsets in these relations differ depending on the oxygenation of the blood. These offsets, while unknown, are constructed using the two given input measures of the applied electrical potentials having known glucose sensitivity relative to the redox reagent system and using an algebraically constructed substitute for the measure of current response, which subtracts the offset based on the oxygen sensitivity and is inserted into the algorithm used to determine the concentration of the analyte. Separating the application of the two DC potentials in time and/or magnitude allows the relative influence of the oxygenation level ($pO_2$) to be sufficiently different for calculation of a correction.

Figure 13:
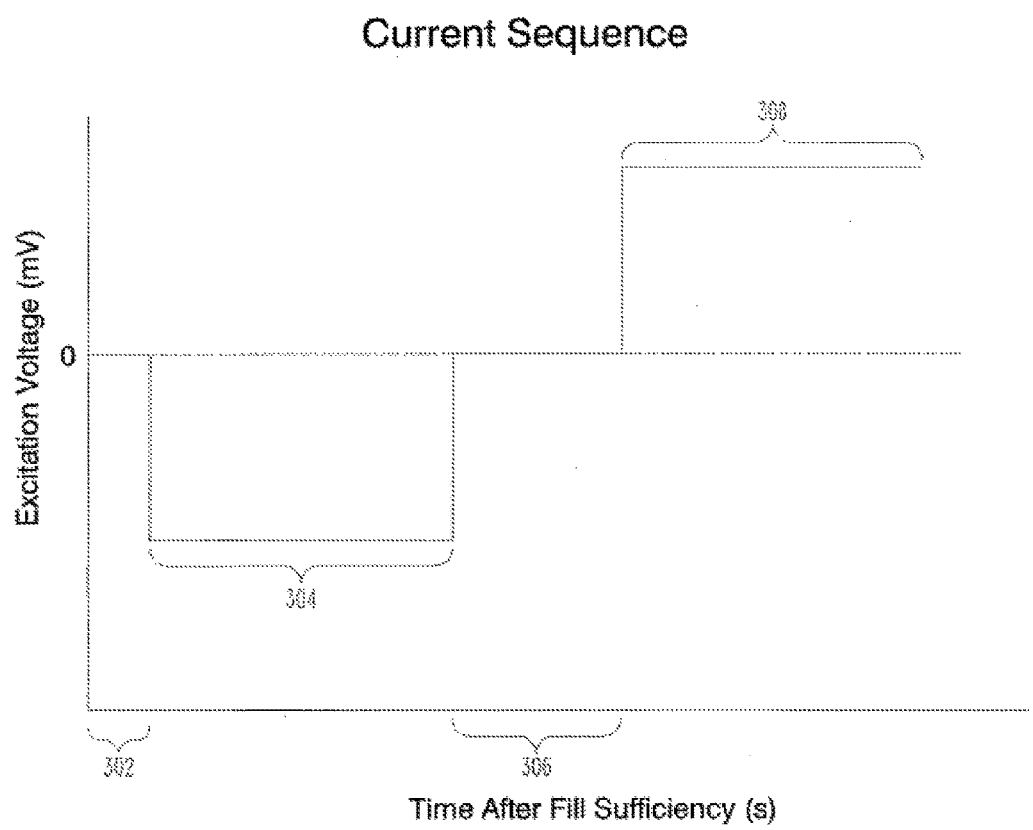
FIG. 13 is a graphical depiction of an excitation potential sequence showing the relationship of excitation potentials to time after a sample has been applied to a biosensor.

Referring again to the test strip embodiment of FIGS. 4-5, after applying a fluid sample to sample chamber 34, two electrode potentials (voltages) are applied to electrodes 22. FIG. 13 depicts an excitation potential sequence showing the relationship of excitation potentials to time after a sample has been applied to a biosensor according to one embodiment of the present invention. During time period 302, no potential is applied, resulting in an effectively open cell, or the potential difference between the electrodes is held or controlled to be effectively zero (in either case of no or controlled potential, referred to as an open cell condition). A first potential 304 is applied following time period 302 and is depicted as having a negative polarity. Following first potential 304, an open cell condition is applied for a time period 306. A second potential 308 is applied following time period 306 and is shown at 308. Second potential 308 is of opposite polarity (positive potential) to the first potential 304. It should be understood that FIG. 13 discloses only one specific embodiment and is not intended to fully disclose the scope of every combination of electrical potentials that may be applied to the biosensor system as disclosed herein. Other excitation potential sequences may be used as would be understood by one of skill in the art.

The current responses to the first potential 304 and the second potential 308 are measured and are then used to calculate the glucose concentration, corrected for blood oxygenation. For example, the measured glucose (GC) for the sample tested with the excitation sequence depicted in FIG. 13 is calculated as: $GC = (coefficient_a)(DC_a) + (coefficient_b)(DC_b)$, where $DC_a$ and $DC_b$ are the current responses of the first potential 304 and the second potential 308, respectively, and $coefficient_a$ and $coefficient_b$ are derived from testing of the reagent layer used in biosensor 20 (see description below for details related to deriving coefficient$_a$ and coefficient$_b$).

To derive the coefficients used to calculate the analyte concentration, testing using the desired test voltage sequence is performed on experimental biosensors similar to biosensor 20. Sample fluids of known analyte concentration are applied to sample chambers of the test-biosensors and the desired sequence of two DC voltages is applied to the sample chamber. A relationship between the actual and measured analyte concentration may then be obtained.

Figure 14:
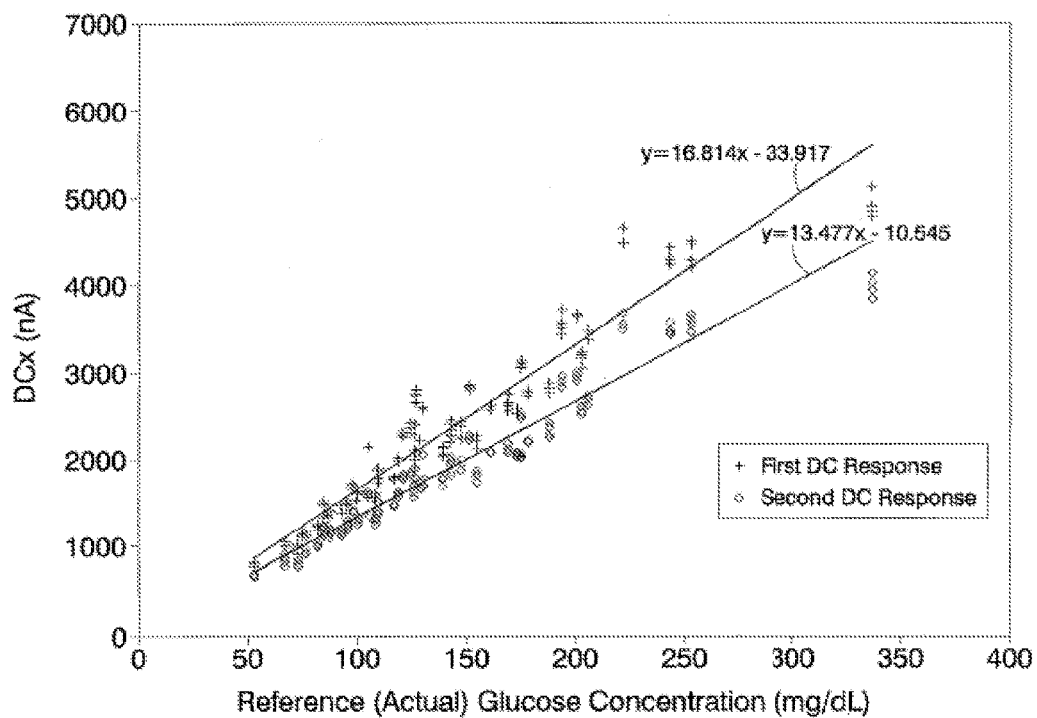
FIG. 14 shows the relation between the first and second DC responses of reference glucose for fresh venous blood, utilizing GOx as an enzyme, and where the test method provides two distinct applications of DC excitation for oxygen compensation.

For example, FIG. 14 depicts the response of experimental biosensors to first and second DC potentials utilizing GOx as an enzyme and fresh venous blood (low oxygenation levels) as the sample fluid. Samples of known glucose concentration are applied, and a linear relationship between current response and glucose concentration is used to curve fit the data. One set of data (approximated by the upper trend line y=16.814x−33.917) represents the first application of DC excitation to the system, and the other set of data (approximated by the lower trend line y=13.477x−10.545) represents the second application of DC excitation to the system.

Figure 15:
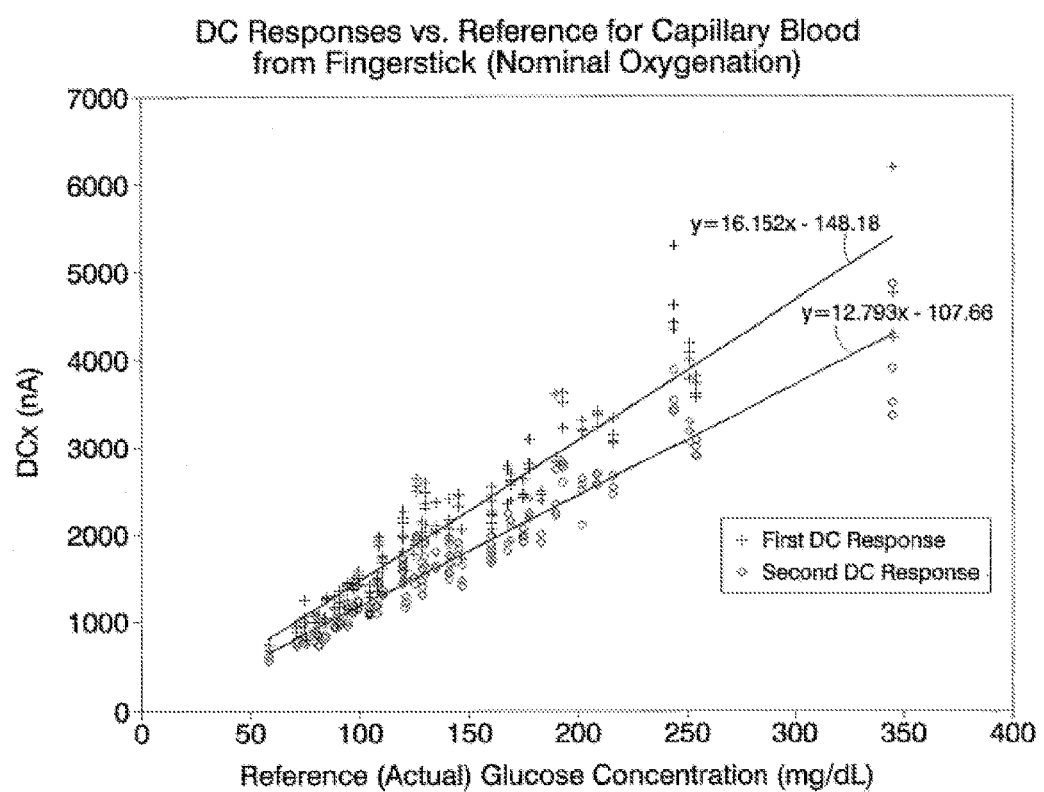
FIG. 15 shows the relation between the first and second DC responses of reference glucose for capillary blood from a finger stick, utilizing GOx as an enzyme, and where the test method provides two distinct applications of DC excitation for oxygen compensation.

FIG. 15 depicts the response of experimental biosensors to the same first and second DC potentials utilizing GOx as an enzyme and blood from finger stick (nominal oxygenation) as the sample fluid. Samples of known glucose concentration are applied, and a linear relationship between response and glucose concentration is again used to curve fit the data. One set of data (approximated by the upper trend line y=16.152x−148.18) represents the first application of DC excitation to the system, and the other set of data (approximated by the lower trend line y=12.793x−107.66) represents the second application of DC excitation to the system.

Figure 16:
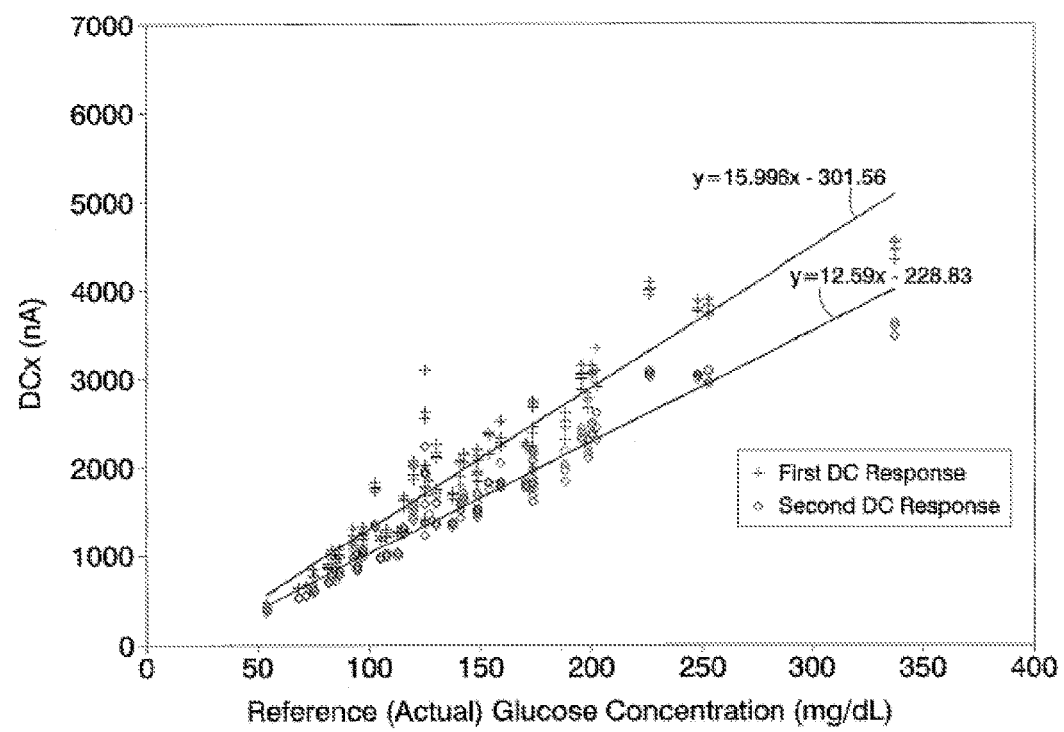
FIG. 16 shows the relation between the first and second DC responses of reference glucose for rocked venous blood, utilizing GOx as an enzyme, and where the test method provides two distinct applications of DC excitation for oxygen compensation.

FIG. 16 depicts another response of experimental biosensors to the same first and second DC potentials utilizing GOx as an enzyme and rocked venous blood (high oxygenation) as the sample fluid. Samples of known glucose concentration are applied, and a linear relationship between response and glucose concentration is again used to curve fit the data. One set of data (approximated by the upper trend line y=15.996x−301.56) represents the first application of DC excitation to the system, and the other set of data (approximated by the lower trend line y=12.59x−228.83) represents the second application of DC excitation to the system.

Again, by assuming a particular relationship (in this case an assumed first-order (linear) relationship) for the data represented in FIGS. 14-16 (as represented by the trend lines in FIGS. 14-16), the correction coefficients can be derived to compensate for the presence of non-analyte reacting compounds (i.e., compounds other than the analyte to be measured such as oxygen) that react with the reagent and would otherwise introduce inaccuracies into the test results. For example, by assuming a linear relationship between the response current and the concentration of the analyte of interest in the sample (e.g., blood glucose concentration), the relationship between the current response to the first DC potential (DC$_a$) and the glucose concentration (GC) may be represented by the following equation:

$$DC_a = \text{intercept}_a + (\text{slope}_a)(GC) \quad (1)$$

where intercept$_a$ is the y-intercept and slope$_a$ is the slope of the trend line of the linear relationship. Similarly, the relationship between the current response to the second DC potential (DC$_b$) and the glucose concentration (GC) may be represented by the following equation:

$$DC_b = \text{intercept}_b + (\text{slope}_b)(\text{glucose}) \quad (2)$$

where intercept$_b$ is the y-intercept and slope$_b$ is the slope of the trend line of the linear relationship.

An algebraic algorithm to compensate for offset error may then be derived. In particular, an algorithm can be derived that creates an interceptless relation that solves for the glucose concentration and compensates for the offset error. For example, given that $$\text{slope}_a / \text{slope}_b = K_1 \quad (3)$$

(where $K_1$ is a constant) and $$\text{intercept}_a / \text{intercept}_b = \text{variable} \quad (4)$$

(where the variable in equation (4) depends on the oxygenation level), and by multiplying both sides of equation (2) by $K_1$, one obtains:

$$(K_1)(DC_b) = (K_1)(\text{intercept}_b) + (K_1)(\text{slope}_b)(GC) \quad (5)$$

thus, substituting slope$_a$=$K_1$ slope$_b$ from (3), $$(K_1)(DC_b) = (K_1)(\text{intercept}_b) + (\text{slope}_a)(GC) \quad (6)$$

and, using equation (1), $$DC_a - (K_1)(DC_b) = [\text{intercept}_a + (\text{slope}_a)(GC)] - [(K_1)(\text{intercept}_b) + (\text{slope}_a)(GC)] \quad (7)$$

Thus, $$DC_a - (K_1)(DC_b) = \text{intercept}_a - (K_1)(\text{intercept}_b) + [(\text{slope}_a)(GC) - (\text{slope}_a)(GC)] \quad (8)$$

which reduces to $$DC_a - (K_1)(DC_b) = \text{intercept}_a - (K_1)(\text{intercept}_b) \quad (9)$$

which is a measure of the oxygenation level influence on the response. Multiplying each side of equation (9) by another constant $K_2$, then adding DC$_a$ to each side of resulting equation and substituting [intercept$_a$+(slope$_a$)(GC)] for DC$_a$ on the right hand side of the resulting equation $$DC_a + K_2[DC_a - K_1(DC_b)] = \text{intercept}_a + \text{slope}_a(GC) + K_2(\text{intercept}_a - K_1(\text{intercept}_b)) \quad (10)$$

and $$DC_a + K_2[DC_a - K_1(DC_b)] = \{\text{intercept}_a + K_2[\text{intercept}_a - K_1(\text{intercept}_b)]\} + \text{slope}_a(GC) \quad (11)$$

by choosing $K_2$ to make the bracketed term in equation (11)—{intercept$_a$+$K_2$[intercept$_a$−$K_1$(intercept$_b$)]}—equal zero $$K_2 = -\text{intercept}_a / [\text{intercept}_a - K_1(\text{intercept}_b)] \quad (12)$$

equation (11) becomes $$DC_a + K_2[DC_a - K_1(DC_b)] = (\text{slope}_a)(GC) \quad (13)$$

solving equation (13) for GC $$GC = \{DC_a + K_2[DC_a - K_1(DC_b)]\} / \text{slope}_a \quad (14)$$

from which follows:

$$GC = (1/\text{slope}_a)(DC_a) + (K_2/\text{slope}_a)(DC_a) - DC_b K_2/[K_1(\text{slope}_a)] \quad (15)$$

and $$GC = [(1+K_2)/\text{slope}_a]DC_a - \{K_2/[K_1(\text{slope}_a)]\}DC_b \quad (16)$$

The GC therefore may be computed as follows:

$$GC = (coefficient_a)(DC_a) + (coefficient_b)(DC_b) \quad (17)$$

where $$coefficient_a = (1+K_2)/slope_a \quad (18)$$

$$coefficient_b = -K_2/[K_1(slope_a)] \quad (19)$$

and $K_1$ and $K_2$ are defined in equations (3) and (12). It will be appreciated that, with the above definitions, $coefficient_a > 0$ and $coefficient_b < 0$.

The above algorithm is an interceptless relation and compensates for the offset error produced by the oxygenation level of the sample. As such, for a given biosensor and reagent layer, the current responses $DC_a$ and $DC_b$ to two test voltages may be used with the previously derived $coefficient_a$ and $coefficient_b$ to determine the concentration of an analyte of interest in a sample deposited into sample chamber 34 of biosensor 20.

It should be appreciated that, although first-order (linear) relationships are used in the example embodiments herein presented, relationships greater than first-order (linear) may be used to curve fit the data obtained by testing samples of known glucose concentration.

Figure 2:
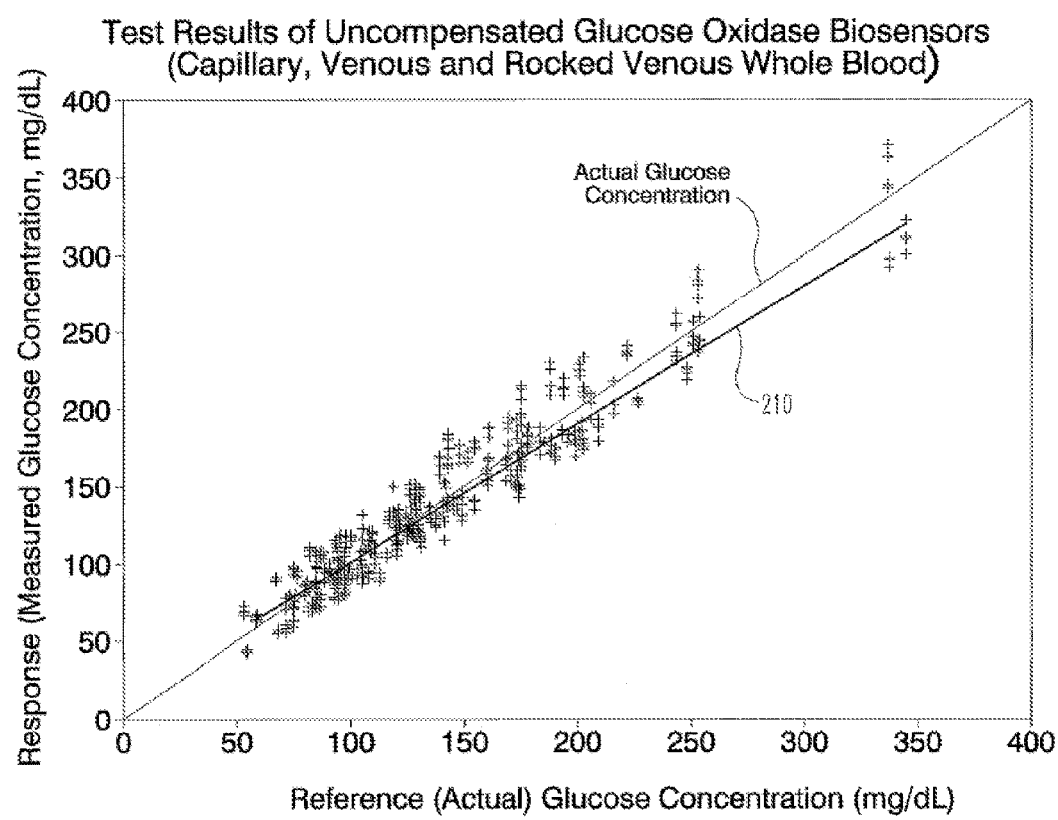
FIG. 2 shows the response and the reference glucose, utilizing GOx as an enzyme, where the biosensor is not compensated as described herein, and the blood sample types are fresh venous blood, capillary blood from a finger stick, and venous blood rocked for ten minutes.
Figure 3:
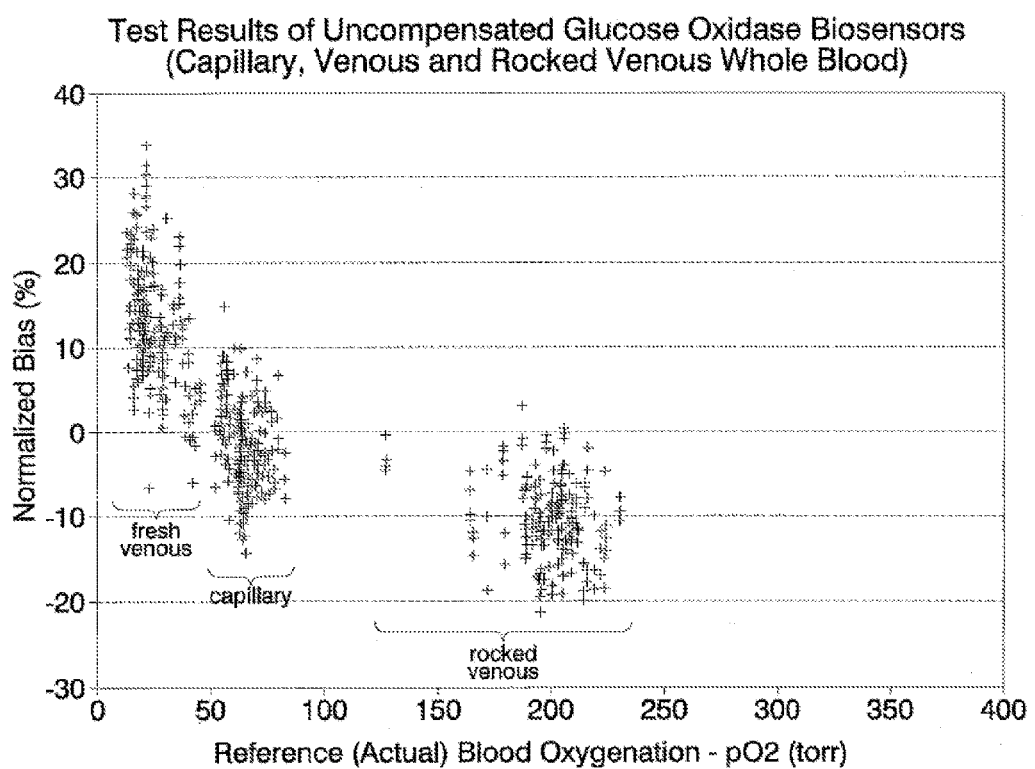
FIG. 3 shows the relationship of normalized bias versus the reference blood oxygenation level for fresh venous, capillary and rocked venous blood for a biosensor that is not compensated as described herein.

To illustrate the difference between using two DC excitations of the sample and traditional test techniques, biosensors with similar test chemistries were used to generate the data in FIGS. 2, 3, 17 and 18. FIGS. 2 and 3 represent biosensors not using the test techniques described herein, while FIGS. 17 and 18 use dual DC excitation test techniques as described herein.

FIG. 2 depicts a comparison between the actual and measured glucose levels using a GOx-based biosensor that does not compensate for oxygenation level. Blood with varying levels of oxygenation was used to obtain the data—fresh venous blood (low oxygenation), capillary blood from a finger stick (nominal oxygenation), and venous blood rocked for 10 minutes (high oxygenation). Trend line 210 (first order curve fit) approximates the test results for capillary (finger stick) blood. Trend line 210 is higher than actual blood glucose levels at lower concentrations (concentrations below approximately 120 mg/dL) and lower than actual blood glucose levels at higher concentrations (concentrations above approximately 120 mg/dL).

FIG. 3 depicts the normalized percent bias of the test data represented in FIG. 2 plotted against actual (reference) oxygenation levels for fresh venous (low $O_2$), capillary (nominal $O_2$) and rocked venous (high $O_2$) test samples. As with FIG. 2, the data in FIG. 3 represents biosensor system bias before oxygenation correction. Table 1 represents select statistical characteristics of the data depicted in FIGS. 2 and 3.

TABLE 1

Statistical Characteristics of FIGS. 2 and 3.

|  | Average of the Normalized Error (avNE) | Standard Deviation of the Normalized Error (sdNE) | Total System Error (TSE) |
| --- | --- | --- | --- |
| Fresh Venous Blood (FV) | 13.3 | 7.24 | 27.8 |
| Capillary-Finger stick (FS) | −1.4 | 5.50 | 12.4 |
| Rocked Venous Blood (RV) | −10.4 | 4.94 | 20.3 |

Figure 17:
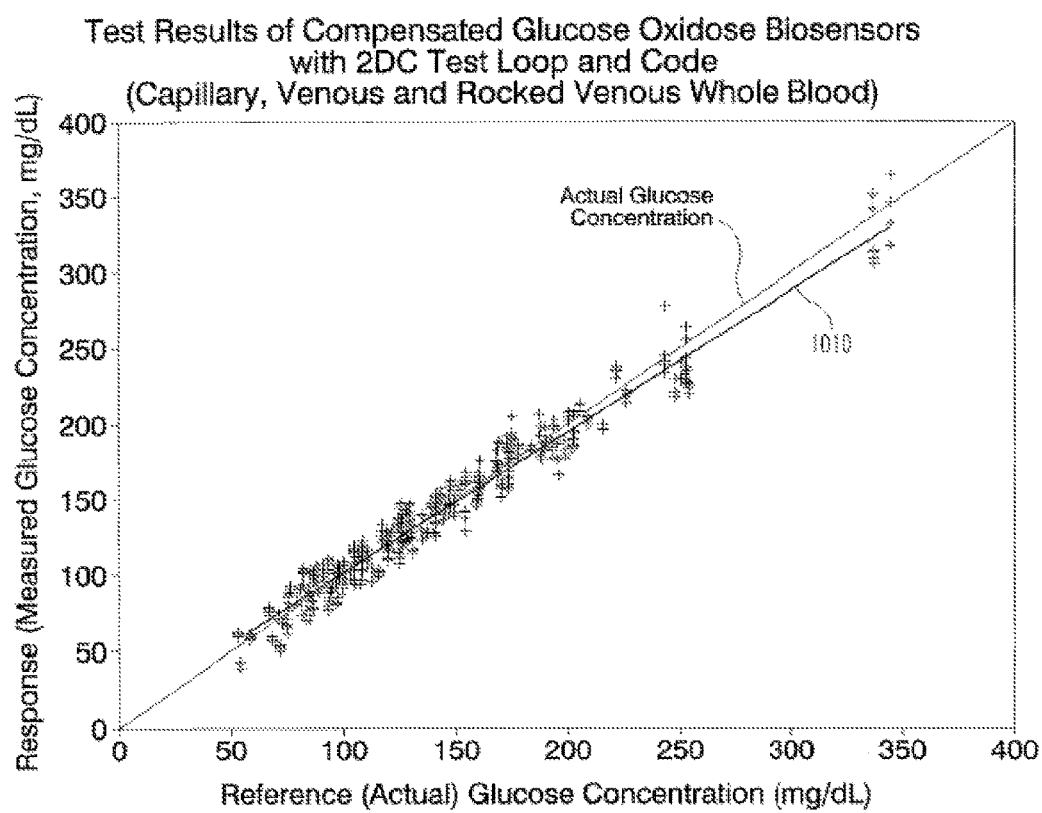
FIG. 17 shows the relationship of the response and the reference glucose, utilizing GOx as an enzyme, where the test method provides two distinct applications of DC excitation for oxygenation compensation, and where the blood sample types are fresh venous blood, capillary blood from a finger stick, and venous blood rocked for ten minutes.

In comparison, FIG. 17 is a plot of the response and the reference glucose, utilizing GOx as an enzyme, where the test method provides two distinct applications of DC excitation for oxygenation compensation, and the two current response measures employ compensation. Blood with varying levels of oxygenation was used to obtain the data—fresh venous blood (low oxygenation), capillary blood from a finger stick (nominal oxygenation), and venous blood rocked for 10 minutes (high oxygenation). Trend line 1010 (first order curve fit) approximates the test results for capillary (finger stick) blood.

Figure 18:
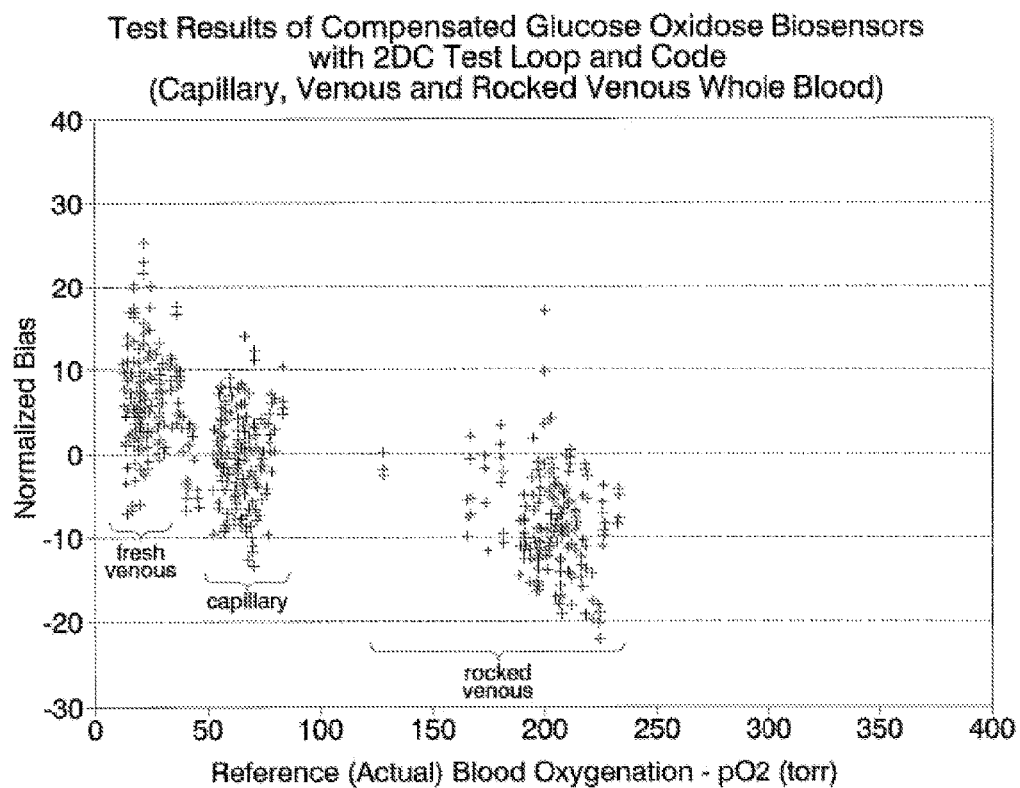
FIG. 18 shows normalized bias versus the reference blood oxygenation level for the data shown in FIG. 17.

FIG. 18 is a plot of normalized bias versus the reference blood oxygenation level for the data shown in FIG. 17. Table 2 represents select statistical characteristics of the data depicted in FIGS. 17 and 18.

TABLE 2

Statistical Characteristics of FIGS. 17 and 18.

|  | Average of the Normalized Error (avNE) | Standard Deviation of the Normalized Error (sdNE) | Total System Error (TSE) |
| --- | --- | --- | --- |
| Fresh Venous Blood (FV) | 6.3 | 5.95 | 18.2 |
| Capillary-Finger stick (FS) | −0.3 | 5.47 | 11.2 |
| Rocked Venous Blood (RV) | −8.4 | 5.67 | 19.7 |

As can be seen by comparing FIGS. 2 and 17, the data for the glucose compensated tests (FIG. 17) is not as dispersed as the data for the uncompensated testing (FIG. 2). Furthermore, trend line 1010 for the data in FIG. 17 is closer to the actual glucose concentration than the trend line 210 for the data in FIG. 2.

The improved result in compensating for oxygenation levels also is evident when comparing Tables 2 and 3. Table 3 represents the improvement realized when using an oxygenation-compensated glucose test (FIGS. 17 and 18, and Table 2) over testing that does not compensate for blood oxygenation (FIGS. 2 and 3, and Table 1).

As an example, the average of the normalized error for rocked venous blood (high oxygenation) without compensating for blood oxygenation is −10.4, while the average of the normalized data for rocked venous blood (high oxygenation) when compensating for blood oxygenation is −8.4—an improvement of 2.0. In fact, a comparison of Tables 1 and 2 reveals that the accuracy (average of the normalized error) of the oxygenation-compensated testing is improved for all levels of blood oxygenation over non-compensated testing. Moreover, with the exception of there being a slight increase in the standard deviation of the normalized error for rocked venous blood (represented by a negative number in Table 3), all of the statistical characteristics for oxygenation-compensated testing (Table 2) are improved over the statistical characteristics for non-compensated testing (Table 1).

TABLE 3

Improvement with Oxygenation Compensation.

|  | Improvement in avNE | Improvement in sdNE | Improvement in TSE |
| --- | --- | --- | --- |
| Fresh Venous Blood (FV) | +7.0 | +1.29 | +9.6 |
| Capillary-Finger stick (FS) | +1.1 | +0.03 | +1.2 |

TABLE 3-continued

Improvement with Oxygenation Compensation.

| | Improvement in avNE | Improvement in sdNE | Improvement in TSE |
|---|---|---|---|
| Rocked Venous Blood (RV) | +2.0 | −0.73 | +0.6 |

Furthermore, the relative bias at high oxygen levels with correction (FIG. 18) is: (−8.4)−(−0.3)=−8.1. By comparison, in FIG. 3 the relative bias at high oxygen levels with no correction is: (−10.4)−(−1.4)=−9. As such, an improvement of 0.9 (9−8.1) is found in the response by compensating for the oxygenation level of sample using the two DC excitations.

Still further, in FIG. 18, the relative bias at low oxygen levels with correction is: 6.3−(−0.3)=6.6. By comparison, in FIG. 3 the relative bias at low oxygen levels without correction is: 13.3−(−1.4)=14.7. As such, an improvement of 8.1 (14.7−6.6) is found in the response by compensating for the oxygenation level of sample using the two DC excitations.

Also shown by a comparison of FIGS. 3 and 18, the overall variation of the results has improved, that is, the data is more compact about a zero bias with the correction for oxygenation. For example, in FIG. 18 the range from the highest average bias (low $pO_2$) to the lowest average bias (high $pO_2$) is: 6.3−(−8.4)=14.7. In contrast, in FIG. 3 the range from the highest average bias (low $pO_2$) to the lowest average bias (high pO2) is: 13.3−(−10.4)=23.7 prior to correction. As such, an overall improvement of 9.0 (23.7−14.7) is found in the response by compensating for the oxygenation level of sample using two DC excitations.

In general, the magnitudes of the voltages applied to the electrodes should be consistent with the chemistries of the biosensor and should be chosen to minimize other negative consequences or offset errors. In certain embodiments, the first and second DC excitations are of differing polarities. In further embodiments, the first and second excitations are of different polarities and are comparable in magnitude. The opposite polarity enables reading of the glucose reaction derived current from different electrodes, and in this manner avoids over utilization of glucose at one electrode, which can create a system unable to accurately resolve very low glucose measurements. Using the same polarity for the excitations can deplete the reagent layer with two measurements being taken on the same layer. Having opposite polarities for the DC excitations appears to be especially beneficial at low glucose levels. By way of example, taking two measurements on the same reagent layer at low blood glucose levels can cause the glucose to be in limited supply on the second measurement, which could result in a flat dose response on the second measurement and degrade the effectiveness of the compensation. Opposite polarity excitations can be less critical at higher glucose levels.

Still further embodiments include applying the DC potential for a very short duration to help avoid depleting the glucose. For example, favorable results can be realized when applying the first DC potential for 4 seconds or less and the second potential for 2 seconds or less.

Still other embodiments include applying first and second DC potentials of approximately 450 mV absolute value to the electrodes. It was discovered that at 450 mV the offset error due to blank current is significantly reduced, where blank current is the diffusion-limited current generated by the oxidation of the reduced form of the mediator at the surface of the working electrode in the absence of enzyme, which can cause offset errors when measuring analyte concentration. In still other embodiments, the first DC potential includes a −450 mV potential being applied to the counter electrode (in essence making it a working electrode) and the second DC potential includes a +450 mV potential being applied to the counter electrode.

An additional advantage of a system and method according to the present invention is that it may be used by those patients with elevated levels of interfering substances in the blood. Certain enzymes, when used in biosensors, will catalyze the analyte for which measurement is desired along with other substances within the fluid sample. In the case of blood glucose meters, for example, the enzyme used in the biosensor is usually chosen for particular specificity with respect to glucose. Avoiding the risk of maltose sensitivity of the biosensor is an important factor in achieving accurate test results. As such, selecting an appropriate enzyme that has insensitivity to maltose is desirable. However, this desirability has been problematic in the past when using certain enzymes because oxygenation in the blood occurs when selecting certain enzymes and results in varying levels of oxygen. As a result, variation in the level of oxygenation of the fluid such as, for example, blood, produces variation in the accuracy of glucose measurements.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A method for determining a concentration of an analyte in a body fluid sample using a reaction involving an enzyme and the analyte, comprising:
    applying a first direct current (DC) pulse of electrical excitation to the body fluid sample in an analyte sensor, the analyte sensor including a first electrode, a second electrode and a reagent, the reagent covering the first electrode and the second electrode, the applying the first DC pulse step including having the first electrode act as a working electrode during the first DC pulse, the first DC pulse generating a first current response;
    measuring the first current response at a plurality of times during the first DC pulse to obtain a first plurality of current measurements;
    determining a reaction rate of the enzyme with the analyte based on the first plurality of current measurements;
    applying a second DC pulse of electrical excitation to the body fluid sample, the applying the second DC pulse step including having the second electrode act as the working electrode during the second DC pulse, the second DC pulse generating a second current response;
    measuring the second current response at a plurality of times during the second DC pulse to obtain a second plurality of current measurements; and
    determining a concentration of the analyte in the body fluid sample based on the second plurality of current measurements compensated for the determined reaction rate.

2. The method of claim 1, further comprising the step of applying a first open cell condition to the body fluid sample between the first and second DC pulses.

3. The method of claim 1, wherein the determined concentration is compensated based on an algorithmic combination of the first and second pluralities of current measurements.

4. The method of claim 1, wherein the first DC pulse has a first absolute voltage magnitude greater than a second absolute voltage magnitude of the second DC pulse to amplify effects of background current.

5. The method of claim 1, wherein the applying the first DC pulse step comprises applying the first DC pulse for a first applying time based on the reaction rate detected from the first current response.

6. The method of claim 5 and further including determining the reaction rate, wherein the duration of the first applying time for the first DC pulse step is shortened or lengthened based on the reaction rate.

7. The method of claim 1, further comprising the step of detecting fill sufficiency of the body fluid sample in the analyte sensor, wherein the applying the first DC pulse step occurs in response to detecting the fill sufficiency of the body fluid sample.

8. The method of claim 7, further comprising the step of delaying the applying the first DC pulse step for an incubation time period after detecting the fill sufficiency of the body fluid sample.

9. The method of claim 1, further comprising the steps of:
applying one or more pulses having an alternating current (AC) component to the body fluid sample in, the analyte sensor; and
measuring one or more AC responses to the pulses, wherein the determining the concentration of the analyte step includes compensating for interferents based on the one or more AC responses.

10. The method of claim 9, wherein the applying the one or more AC pulses step occurs between the first DC pulse and the second DC pulse.

11. The method of claim 1, wherein the determining the concentration of the analyte step compensates for variable reaction velocity of the enzyme.

12. The method of claim 1, further comprising determining the reaction rate from a time-to-peak for the first current response based on the first plurality of current measurements.

13. The method of claim 1, further comprising determining the reaction rate from the shape of the, first current response based on the first plurality of current measurements.

14. A method for determining a concentration of an analyte in a body fluid sample using a reaction involving an enzyme and the analyte, the method comprising measuring the current responses to first and second applied direct current (DC) pulses, comprising:
applying a first DC pulse of electrical excitation to the body fluid sample in an analyte sensor, the first DC pulse generating a first current response corresponding to the reaction of the enzyme with the analyte;
measuring the first current response during the first DC pulse to obtain a first current measurement;
determining a reaction rate for the reaction of the enzyme with the analyte using the first current measurement;
applying a second DC pulse of electrical excitation to the body fluid sample, the second DC pulse generating a second current response;
measuring the second current response during the second. DC pulse to obtain a second current measurement; and
determining a concentration of the analyte in the body fluid sample using the second current measurement, said determining including using an algorithm that varies, depending on reaction rate of the enzyme and the analyte, said determining further including adjusting the algorithm based on the determined reaction rate.

15. The method, of claim 14 in which the algorithm includes coefficients that vary depending on reaction rate, said determining including applying coefficients corresponding to the determined reaction rate.

16. The method of claim 14, further comprising the step of applying a first open cell condition to the body fluid sample between the first and second DC pulses.

17. The method of claim 14, wherein the determined concentration is compensated based on an algorithmic combination of the first and second pluralities of current measurements.

18. The method of claim 14, wherein the first DC pulse has a first absolute voltage magnitude greater than a second absolute voltage magnitude of the second DC pulse to amplify effects of background current.

19. The method of claim 14, wherein the applying the first DC pulse step comprises applying the first DC pulse for a first applying time based on the reaction rate detected from the first current response.

20. The method of claim 19 and further including determining the reaction rate, wherein the duration of the first applying time for the first DC pulse step is shortened or lengthened based on the reaction rate.

21. The method of claim 14, further comprising the step of detecting fill sufficiency of the body fluid sample in the analyte sensor, wherein the applying the first DC pulse step occurs in response to detecting the fill sufficiency of the body fluid sample.

22. The method of claim 21, further comprising the step of delaying the applying the first DC pulse step for an incubation time period after detecting the fill sufficiency of the body fluid sample.

23. The method of claim 14, further comprising the steps of:
applying one or more pulses having an alternating current (AC) component to the body fluid sample in the analyte sensor; and
measuring one or more AC responses to the pulses, wherein the determining the concentration of the analyte step includes compensating for interferents based on the one or more AC responses.

24. The method of claim 23, wherein the applying the one or more AC pulses step occurs between the first DC pulse and the second DC pulse.

25. The method of claim 14, wherein the determining the concentration of the analyte step compensates for variable reaction velocity of the enzyme.

26. The method of claim 14, further comprising determining the reaction rate from a time-to-peak for the first current response based on the first plurality of current measurements.

27. The method of claim 14, further comprising determining the reaction rate from the shape of the first current response based on the first plurality of current measurements.

* * * * *